(12) United States Patent
Yoshida et al.

(10) Patent No.: US 11,931,099 B2
(45) Date of Patent: Mar. 19, 2024

(54) CATHETER FLEXIBLE PRINTED WIRING BOARD AND METHOD FOR MANUFACTURING THE SAME

(71) Applicant: NIPPON MEKTRON, LTD., Tokyo (JP)

(72) Inventors: Akio Yoshida, Tokyo (JP); Ryoichi Toyoshima, Tokyo (JP); Mitsunori Sasaki, Tokyo (JP); Hiroyasu Hasegawa, Tokyo (JP)

(73) Assignee: NIPPON MEKTRON, LTD., Tokyo (JP)

( * ) Notice: Subject to any disclaimer, the term of this patent is extended or adjusted under 35 U.S.C. 154(b) by 1467 days.

(21) Appl. No.: 16/246,695

(22) Filed: Jan. 14, 2019

(65) Prior Publication Data
US 2019/0239946 A1 Aug. 8, 2019

(30) Foreign Application Priority Data

Feb. 5, 2018 (JP) ................................ 2018-018303

(51) Int. Cl.
*H05K 1/11* (2006.01)
*A61B 18/14* (2006.01)
*H05K 1/18* (2006.01)

(52) U.S. Cl.
CPC ............ *A61B 18/1492* (2013.01); *H05K 1/11* (2013.01); *H05K 1/118* (2013.01); *H05K 1/18* (2013.01); *H05K 2201/09027* (2013.01); *H05K 2201/09236* (2013.01); *H05K 2201/09281* (2013.01); *H05K 2201/09827* (2013.01); *H05K 2201/10151* (2013.01)

(58) Field of Classification Search
CPC ..... A16B 18/1492; H05K 2201/09727; H05K 2201/09154; H05K 2201/09027; H05K 2201/09237; H05K 2201/09281; H05K 2201/09827
See application file for complete search history.

(56) References Cited

U.S. PATENT DOCUMENTS

| 4,697,143 A | * | 9/1987 | Lockwood | ......... G01R 1/06772 |
| | | | | 324/762.05 |
| 6,518,663 B1 | * | 2/2003 | James | ..................... H05K 1/025 |
| | | | | 257/691 |
| 7,632,236 B2 | | 12/2009 | Kaneto et al. | |
| 2002/0075093 A1 | * | 6/2002 | Mauritz | .................. H01P 5/028 |
| | | | | 333/263 |
| 2003/0020564 A1 | * | 1/2003 | Nishimura | ........... H03H 9/0207 |
| | | | | 333/187 |

(Continued)

FOREIGN PATENT DOCUMENTS

| JP | H09-061262 A | 3/1997 |
| JP | H09-308638 A | 12/1997 |

(Continued)

*Primary Examiner* — Paresh Paghadal
(74) *Attorney, Agent, or Firm* — Studebaker & Brackett PC

(57) ABSTRACT

A catheter flexible printed wiring board which includes: a long flexible insulating base member having a tip end portion and a base end portion; and a conductive pattern formed on the flexible insulating base member and extending from the base end portion to the tip end portion, wherein the conductive pattern at the base end portion is wider than the conductive pattern at the tip end portion and thicker than the conductive pattern at the tip end portion.

9 Claims, 14 Drawing Sheets

(56) References Cited

U.S. PATENT DOCUMENTS

| | | | | |
|---|---|---|---|---|
| 2003/0091258 A1* | 5/2003 | Uesaka | ............... | H01P 5/08 |
| | | | | 385/2 |
| 2003/0214364 A1* | 11/2003 | Cites | ............... | H01P 5/08 |
| | | | | 333/33 |
| 2005/0133922 A1* | 6/2005 | Fjelstad | ............... | H01L 23/13 |
| | | | | 257/E23.07 |
| 2006/0055021 A1* | 3/2006 | Yamamoto | ............... | H01L 23/4985 |
| | | | | 257/E21.503 |
| 2006/0087379 A1* | 4/2006 | Bartley | ............... | H01P 5/02 |
| | | | | 333/34 |
| 2006/0129061 A1 | 6/2006 | Kaneto et al. | | |
| 2006/0226930 A1* | 10/2006 | Carvalho | ............... | H01P 5/02 |
| | | | | 333/34 |
| 2008/0283289 A1* | 11/2008 | He | ............... | H05K 1/025 |
| | | | | 174/268 |
| 2009/0284324 A1* | 11/2009 | Van Quach | ............... | H05K 1/0237 |
| | | | | 333/34 |
| 2015/0029073 A1* | 1/2015 | Tien | ............... | H01Q 1/50 |
| | | | | 343/863 |
| 2017/0131809 A1* | 5/2017 | Lin | ............... | G06F 1/1652 |
| 2017/0288290 A1* | 10/2017 | Oster | ............... | H01B 11/1891 |

FOREIGN PATENT DOCUMENTS

| | | | |
|---|---|---|---|
| JP | 2002333412 A | * | 11/2002 |
| JP | 2006-167119 A | | 6/2006 |
| JP | 2006-325985 A | | 12/2006 |
| JP | 5253535 B2 | | 7/2013 |
| JP | 2017-037988 A | | 2/2017 |

* cited by examiner

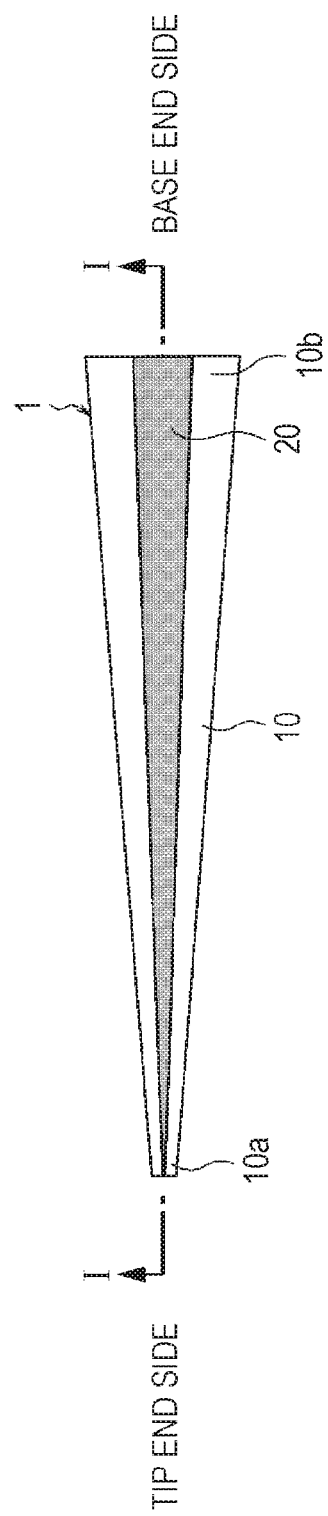

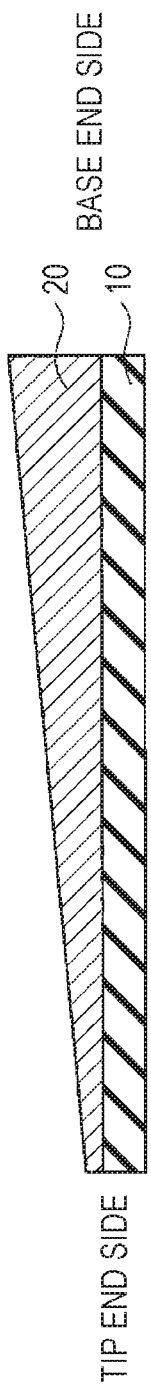

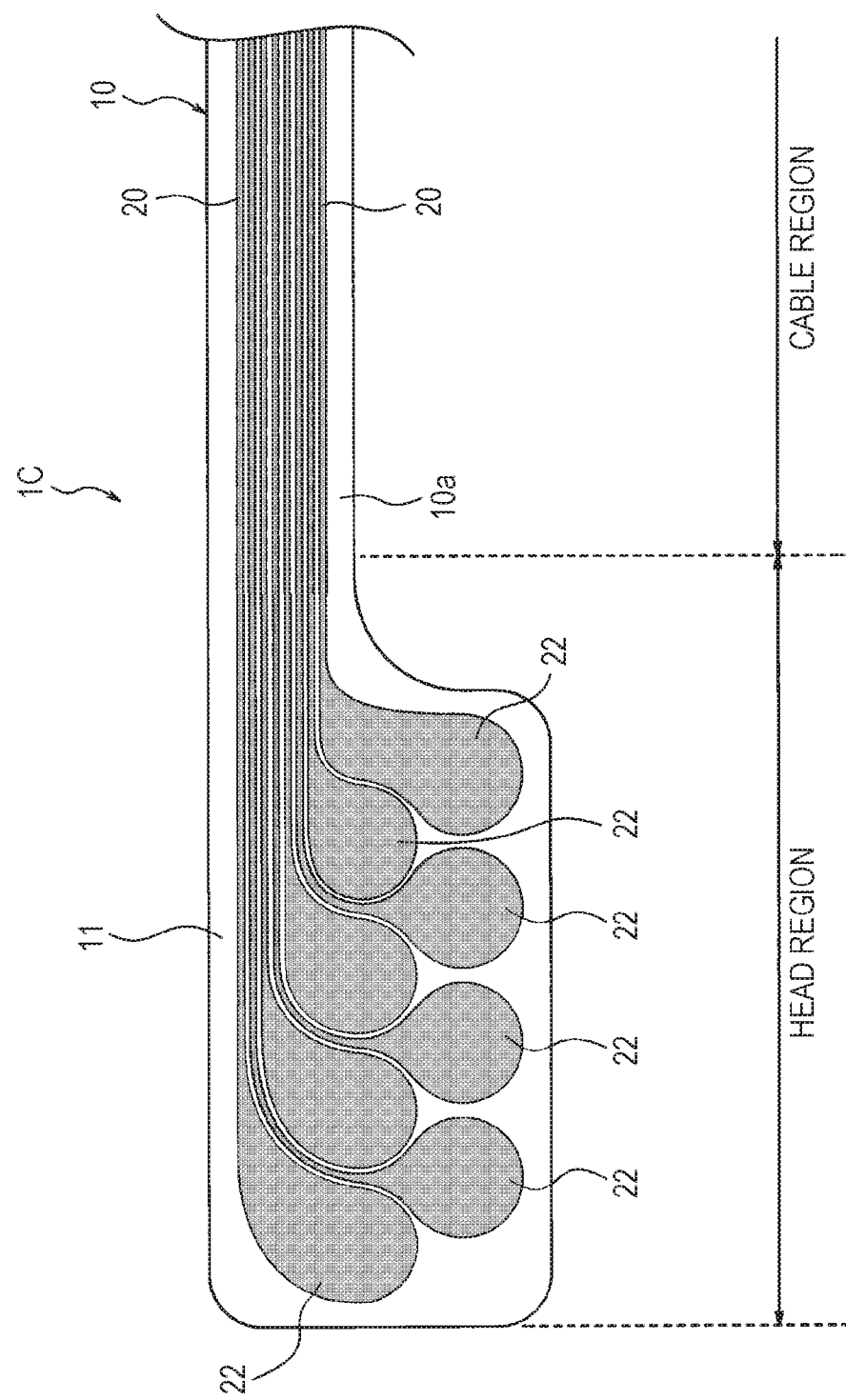

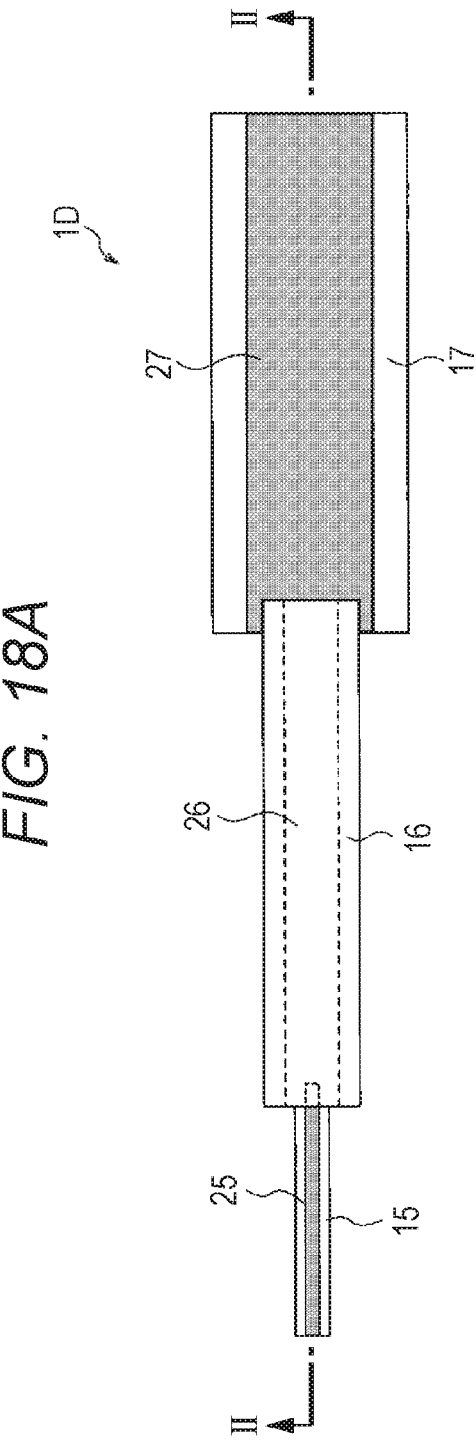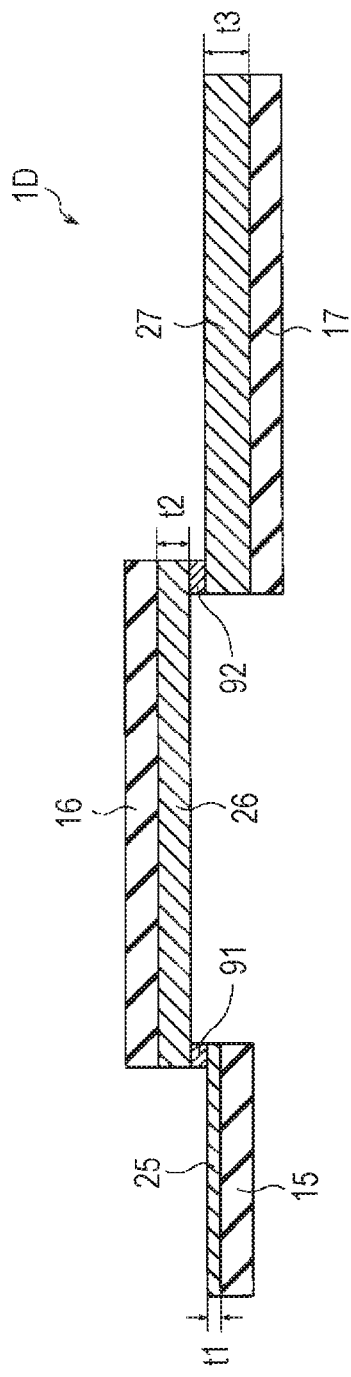

CATHETER FLEXIBLE PRINTED WIRING BOARD AND METHOD FOR MANUFACTURING THE SAME

CROSS-REFERENCE TO RELATED APPLICATION

This application claims priority from Japanese Patent Application No. 2018-018303 filed with the Japan Patent Office on Feb. 5, 2018, the entire content of which is hereby incorporated by reference.

BACKGROUND

1. Technical Field

The present disclosure relates to a catheter flexible printed wiring board.

2. Related Art

A flexible printed wiring board for a catheter used inserted into a body for diagnosis or treatment has been known. More specifically, a flexible printed wiring board inserted into a flexible tube and used as a single component forming a catheter and the method for the flexible printed wiring board has been known.

JP-A-9-308638 and Japanese Patent No. 5253535 describe an electrode catheter (also called an ablation catheter) used for, e.g., treatment for abnormal cardiac rhythm. An electrode for applying high-frequency current to ablate a body tissue is provided at a tip end of the electrode catheter. According to the electrode catheter described in JP-A-9-308638, the electrode is electrically connected to a high-frequency generation device via a conductive wire. According to the electrode catheter described in Japanese Patent No. 5253535, an FPC substrate (also called a flexible substrate or a flexible printed wiring board) is arranged in an insulating tube member. A contact layer formed on the FPC substrate forms a ring-shaped electrode. Note that the electrode at the tip end is connected to a conductive wire as in JP-A-9-308638.

JP-A-2006-325985 describes an inspection catheter for extracting, as inspection signals, biochemical data and physiological data on the inside of a living body. The inspection catheter has, at a tip end portion thereof, a flexible substrate on which an inspection electrode is provided. The flexible substrate is provided only at a tip end portion of the catheter. The inspection electrode is electrically connected to an external device via a conductive wire (an enamel wire).

SUMMARY

A catheter flexible printed wiring board according to an embodiment of the present disclosure includes a long flexible insulating base member having a tip end portion and a base end portion; and a conductive pattern formed on the flexible insulating base member and extending from the base end portion to the tip end portion, wherein the conductive pattern at the base end portion is wider than the conductive pattern at the tip end portion and thicker than the conductive pattern at the tip end portion.

BRIEF DESCRIPTION OF THE DRAWINGS

FIG. 1 is a plan view of a catheter flexible printed wiring board according to a first embodiment;

FIG. 2 is a sectional view along an I-I line of FIG. 1;

FIG. 17 is a plan view of a catheter flexible printed wiring board according to a second embodiment;

FIG. 18A is a plan view of a catheter flexible printed wiring board according to a third embodiment; and FIG. 18B is a sectional view along an II-II line of FIG. 18A.

DETAILED DESCRIPTION

Figure 3A:
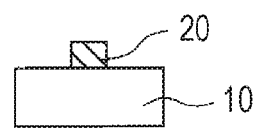
FIG. 3A is a view of the catheter flexible printed wiring board of the first embodiment from a tip end side.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Considering thinning of the catheter and mounting of various sensors on the tip end portion, not the conductive wire (a hair wire) but the flexible printed wiring board is preferably used for electrical connection. In the case of using the flexible printed wiring board, when an attempt is made to thin the catheter, a wire (a conductive pattern) needs to be thinned. Moreover, for realizing a multifunction catheter, the number of wires needs to be increased. Thus, in this case, the wire also needs to be thinned.

However, when the wire is thinned, wiring resistance increases. An increase in the wiring resistance is not preferable specifically for use for the ablation catheter. This is because the catheter is long and relatively-great high-frequency current needs to be applied to the electrode at the tip end portion. Thus, for the catheter flexible printed wiring board, both of thinning of the wire and reduction in the wiring resistance have been demanded.

For reducing the wiring resistance, the thickness of the wire might be increased. However, when the section of the wire becomes too vertically long, structural stability of the wire might be lowered.

When the flexible printed wiring board is applied only to the tip end portion as in JP-A-2006-325985, the wiring resistance can be reduced as a whole. However, there is a problem that the effort for connecting the flexible printed wiring board and the conductive wire is required. Further, a connection portion between the flexible printed wiring board and the conductive wire is arranged in the flexible tube. Thus, upon, e.g., use of the catheter, connection failure might occur.

The present disclosure is for handling the above-described technical problems. That is, an object of the present disclosure is to provide a catheter flexible printed wiring board configured so that the width of a tip end portion of a conductive pattern can be narrowed and a resistance value of the conductive pattern can be reduced and provide the method for manufacturing the catheter flexible printed wiring board.

A catheter flexible printed wiring board according to the present disclosure includes a long flexible insulating base member having a tip end portion and a base end portion; and a conductive pattern formed on the flexible insulating base member and extending from the base end portion to the tip end portion, wherein the conductive pattern at the base end portion is wider than the conductive pattern at the tip end portion and thicker than the conductive pattern at the tip end portion.

In the catheter flexible printed wiring board, a width of the conductive pattern may increase from the tip end portion toward the base end portion, and a thickness of the conductive pattern increases from the tip end portion toward the base end portion.

In the catheter flexible printed wiring board, a thickness of the conductive pattern at the tip end portion may be equal to or less than 1.5 times as large as a width of the conductive pattern at the tip end portion.

In the catheter flexible printed wiring board, a width of the flexible insulating base member may decrease from the base end portion toward the tip end portion.

In the catheter flexible printed wiring board, an electrode may be attached to a tip end of the conductive pattern, and a pad electrically connected to a high-frequency generation device may be provided at a base end of the conductive pattern.

The catheter flexible printed wiring board may further include a head portion having a pad for mounting a sensor, wherein the head portion extends from the tip end portion, and the pad is electrically connected to the conductive pattern.

In the catheter flexible printed wiring board, a first conductive pattern and a second conductive pattern may be, as the conductive pattern, formed on the flexible insulating base member, and an interval between the first conductive pattern and the second conductive pattern may be substantially constant.

In the catheter flexible printed wiring board, a first conductive pattern and a second conductive pattern may be, as the conductive pattern, formed on the flexible insulating base member, and an interval between the first conductive pattern and the second conductive pattern may decrease from the base end portion toward the tip end portion.

In the catheter flexible printed wiring board, the flexible insulating base member may be integrally formed.

In the catheter flexible printed wiring board, the flexible insulating base member may have a first partial flexible insulating base member and a second partial flexible insulating base member, a first partial conductive pattern formed on the first partial flexible insulating base member may have a first thickness, a second partial conductive pattern formed on the second partial flexible insulating base member and electrically connected to the first partial conductive pattern may have a second thickness greater than the first thickness, and the first partial conductive pattern and the second partial conductive pattern may form the conductive pattern.

A catheter flexible printed wiring board manufacturing method includes a step of preparing a long flexible insulating base member having a tip end portion and a base end portion and having a seed layer on a surface, a step of patterning a resist layer formed on the seed layer to form a resist mask provided with an opening extending from the tip end portion to the base end portion, a width of the opening at the base end portion being greater than a width of the opening at the tip end portion; a step of forming a plated layer on the seed layer exposed in the opening of the resist mask such that a plating thickness at the base end portion is greater than a plating thickness at the tip end portion; and a step of removing the resist mask and the seed layer therebelow.

In the catheter flexible printed wiring board manufacturing method, a horizontally-conveying web plating equipment having multiple cells continuously provided along a predetermined direction and configured such that the entire length of the multiple cells is the same as that of the flexible insulating base member is used to form the plated layer.

In the catheter flexible printed wiring board manufacturing method, the step of forming the plated layer may include conveying the flexible insulating base member into the horizontally-conveying web plating equipment having multiple cells from the base end portion side, and taking the flexible insulating base member directly out of the horizontally-conveying web plating equipment promptly after plating current is stopped when the base end portion reaches a downstreammost one of the multiple cells, wherein the plurality of cells may be continuously provided along a predetermined direction, and an entire length of the multiple cells may be equal to or longer than a length of the flexible insulating base member.

In the catheter flexible printed wiring board manufacturing method, the step of forming the plated layer may include forming the plated layer simultaneously at each cell by a roll-to-roll method using the horizontally-conveying web plating equipment, wherein the horizontally-conveying web plating equipment may have multiple cells continuously provided along a flow direction, and each width of the multiple cells may be equal to or longer than a width of a roll-shaped flexible insulating base member equivalent to multiple flexible insulating base members connected to each other at a predetermined interval with a lateral direction thereof being along the flow direction.

In the catheter flexible printed wiring board manufacturing method, the step of forming the plated layer may include using a separated sheet plating equipment having a cell extending in a predetermined direction and multiple anode electrodes provided along the predetermined direction in the cell, arranging, in the cell, the flexible insulating base member negatively charged, and applying different positive voltages to the multiple anode electrodes such that a plating current density increases from a tip end portion side toward the base end portion side.

In the catheter flexible printed wiring board manufacturing method, the step of forming the plated layer may comprise using a separated sheet plating equipment having a cell extending in a predetermined direction and an anode electrode, wherein the anode electrode is provided inclined with respect to the flexible insulating base member disposed in the cell such that the distance to the flexible insulating base member decreases from the tip end portion side toward the base end portion side.

A catheter flexible printed wiring board manufacturing method according to the present disclosure includes a step of preparing a long flexible insulating base member having a tip end portion and a base end portion and a metal-clad laminate having metal foil on a surface of the flexible insulating base member; a step of forming a resist mask extending from the tip end portion to the base end portion on the metal foil and having a greater width at the base end portion than a width at the tip end portion; an etching step of removing, by etching, a portion of the metal foil uncovered with the resist mask; and a step of removing the resist mask, wherein the etching step includes etching the metal foil such that a thickness of the metal foil at the base end portion is greater than a thickness of the metal foil at the tip end portion.

In the catheter flexible printed wiring board according to the present disclosure, the conductive pattern extends from the base end portion to the tip end portion of the long flexible insulating base member. Moreover, the conductive pattern at the base end portion is formed wider than the conductive pattern at the tip end portion and thicker than the conductive pattern at the tip end portion. Thus, according to the present disclosure, the width of the tip end portion of the conductive pattern can be narrowed while the resistance value of the conductive pattern can be reduced.

Hereinafter, embodiments according to the present disclosure will be described with reference to the drawings. Note that in each figure, the same reference numerals are used to represent components having equivalent functions. Moreover, the drawings are schematically illustrated. For example, a relationship between a thickness and a planar dimension and a thickness ratio of each layer are different from actual relationship and ratio.

First Embodiment

Figure 3B:
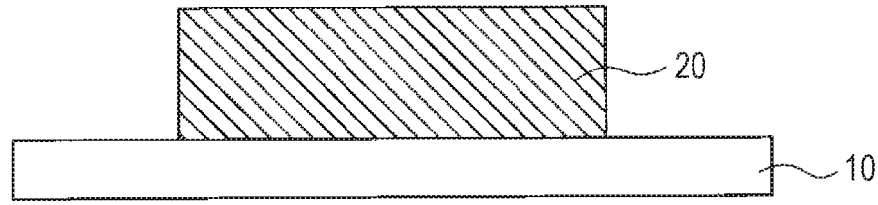
FIG. 3B is a view of the catheter flexible printed wiring board of the first embodiment from a base end side.

A catheter flexible printed wiring board 1 according to a first embodiment of the present disclosure will be described with reference to FIGS. 1 to 3. FIG. 1 is a plan view of the catheter flexible printed wiring board 1. FIG. 2 is a sectional view along an I-I line of FIG. 1. FIG. 3A is a view of the catheter flexible printed wiring board 1 from a tip end side. FIG. 3B is a view of the catheter flexible printed wiring board 1 from a base end side.

The catheter flexible printed wiring board 1 includes a long flexible insulating base member 10 having a tip end portion 10a and a base end portion 10b, and a conductive pattern 20 formed on the flexible insulating base member 10 and extending from the base end portion 10b toward the tip end portion 10a. Note that the tip end portion 10a is a catheter flexible printed wiring board 1 side to be inserted into a human body.

The catheter flexible printed wiring board 1 is used as a single component which is to be inserted into a flexible tube (not shown) and which forms a catheter.

As illustrated in FIG. 1, the catheter flexible printed wiring board 1 includes, as a base material, the single flexible insulating base member 10. That is, the flexible insulating base member 10 is integrally formed. In other words, the flexible insulating base member 10 does not have a configuration including multiple flexible printed wiring boards connected to each other along a longitudinal direction.

The flexible insulating base member 10 is made of an insulating material having flexibility, such as polyimide. Note that the insulating material is not limited to polyimide. A well-known insulating material can be used as the base material of the flexible printed wiring board. Examples of available materials include polyamide, polyethylene naphthalate (PEN), polyethylene terephthalate (PET), and liquid crystal polymer (LCP).

As illustrated in FIG. 1, the flexible insulating base member 10 is formed narrower from the base end portion 10b toward the tip end portion 10a. Thus, a catheter having a thinner tip end than that of a typical hair wire can be provided. For example, the width of the flexible insulating base member 10 at the tip end portion 10a is equal to or less than 1.0 mm. The length of the flexible insulating base member 10 depends on use. The width of the flexible insulating base member 10 is about several tens of cm to 2 m, for example. Note that the width of the flexible insulating base member 10 may be constant.

The conductive pattern 20 is made of a conductive material such as copper foil. The conductive material is not limited to such a material, and other materials (e.g., silver or aluminum) may be employed.

As illustrated in FIG. 1, the conductive pattern 20 is formed wider from the tip end portion 10a to the base end portion 10b. Moreover, as illustrated in FIGS. 2, 3A, and 3B, the conductive pattern 20 is formed thicker from the tip end portion 10a toward the base end portion 10b. For example, the thickness of the conductive pattern 20 at the tip end portion 10a is 5 to 20 μm. Moreover, the thickness of the conductive pattern 20 at the base end portion 10b is 25 to 60 μm.

In the present application, the conductive pattern formed wider as extending from the tip end portion 10a toward the base end portion 10b includes not only a conductive pattern smoothly widened, but also a conductive pattern widened in a stepwise manner. As long as the conductive pattern is widened from a broad point of view, the conductive pattern may be locally narrowed. Generally, the conductive pattern at the base end portion 10b is wider than the conductive pattern at the tip end portion 10a.

Moreover, in the present application, the conductive pattern formed thicker from the tip end portion toward the base end portion includes not only a conductive pattern smoothly thickened, but also a conductive pattern thickened in a stepwise manner. As long as the conductive pattern is thickened from a broad point of view, the conductive pattern may be locally thinned. Generally, the conductive pattern 20 at the base end portion 10b is thicker than the conductive pattern 20 at the tip end portion 10a.

Note that the thickness of the conductive pattern 20 at the tip end portion 10a is preferably equal to or less than 1.5 times as large as the width of the conductive pattern 20 at the tip end portion 10a, and more preferably equal to or less than 1.0 times. Thus, structural stability of the conductive pattern 20 can be ensured. Further, a failure such as falling of the conductive pattern 20 with the thin tip end portion 10a can be reduced.

As described above, in the first embodiment, the conductive pattern 20 at the base end portion 10b is wider than the conductive pattern 20 at the tip end portion 10a and thicker than the conductive pattern 20 at the tip end portion 10a. Thus, according to the first embodiment, the width of the conductive pattern 20 at the tip end portion 10a can be narrowed while a resistance value of the conductive pattern 20 can be reduced. In other words, even in a case where the width of the conductive pattern 20 at the tip end portion 10a is narrowed, the resistance value of the conductive pattern 20 can be reduced. As a result, the resistance value of the conductive pattern 20 can be reduced while the line of the conductive pattern 20 at the tip end portion 10a can be narrowed. Further, according to the first embodiment, it is not necessary to use a conductive wire such as a hair wire for electrical connection. Thus, the steps of connecting and mounting the conductive wire can be eliminated. As a result, manufacturability of the catheter can be improved.

In addition, according to the first embodiment, a conductive wire connection portion is eliminated. Thus, occurrence of connection failure can be reduced. Consequently, reliability of the catheter can be improved.

Figure 4:
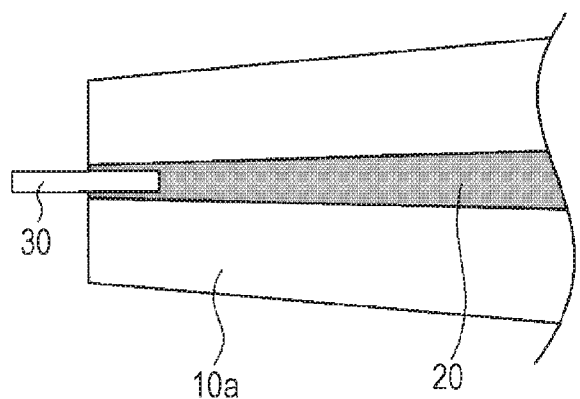
FIG. 4 is a plan view of a tip end portion of a catheter flexible printed wiring board applied to ablation.
Figure 5:
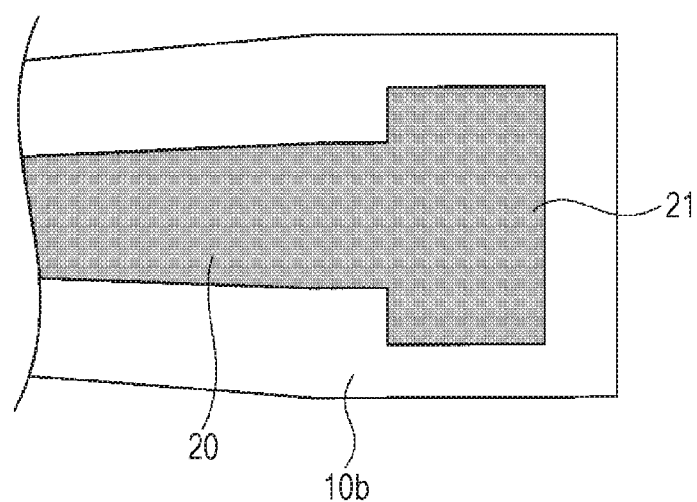
FIG. 5 is a plan view of a base end portion of the catheter flexible printed wiring board applied to ablation.

As described above, according to the present embodiment, low-resistance of the conductive pattern 20 can be realized. Thus, the catheter flexible printed wiring board 1 is suitable for use for an ablation catheter. In this case, as illustrated in FIG. 4, an electrode 30 for ablation of a body tissue of, e.g., the heart is attached to a tip end portion of the conductive pattern 20. Moreover, as illustrated in FIG. 5, a pad 21 electrically connected to a high-frequency generation device (not shown) is provided on the base end side of the conductive pattern 20. Since the flexible printed wiring board is used, the shape of the pad 21 (a terminal) can be freely set. Moreover, it is not necessary to insert, as in a typical case, a conductive wire such as a hair wire into a hole of a connector pin by means of a magnifying glass to perform soldering. That is, the conductive pattern 20 and an external device such as the high-frequency generation device can be electrically connected to each other via an easily-insertable/removable FPC connector (not shown).

Next, two variations according to the first embodiment will be described. Any of these variations can provide advantageous effects similar to those of the first embodiment.

<First Variation>

Figure 6:
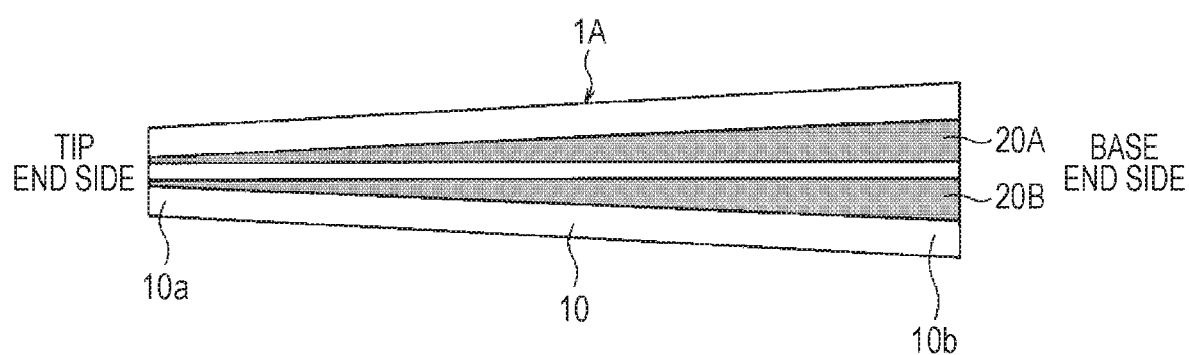
FIG. 6 is a plan view of a catheter flexible printed wiring board according to a first variation of the first embodiment.

As illustrated in FIG. 6, a catheter flexible printed wiring board 1A according to the present variation is configured such that two conductive patterns 20A, 20B are formed on the flexible insulating base member 10. The conductive pattern 20A and the conductive pattern 20B extend substantially parallel to each other from the base end portion 10b toward the tip end portion 10a of the flexible insulating base member 10.

The conductive pattern 20A at the base end portion 10b is wider than the conductive pattern 20A at the tip end portion 10a and thicker than the conductive pattern 20A at the tip end portion 10a. Similarly, the conductive pattern 20B at the base end portion 10b is wider than the conductive pattern 20B at the tip end portion 10a and thicker than the conductive pattern 20B at the tip end portion 10a.

The conductive pattern 20A and the conductive pattern 20B are formed such that an interval therebetween is constant as illustrated in FIG. 6. For such formation, manufacturing by a semi-additive method is suitable as described later.

<Second Variation>

Figure 7:
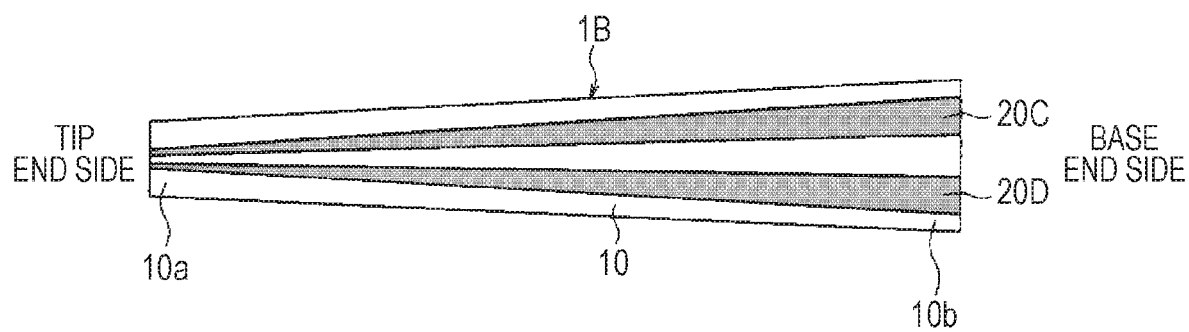
FIG. 7 is a plan view of a catheter flexible printed wiring board according to a second variation of the first embodiment.

As illustrated in FIG. 7, a catheter flexible printed wiring board 1B according to the present variation is configured such that two conductive patterns 20C, 20D are formed on the flexible insulating base member 10. The conductive pattern 20C and the conductive pattern 20D extend from the base end portion 10b to the tip end portion 10a of the flexible insulating base member 10.

The conductive pattern 20C at the base end portion 10b is wider than the conductive pattern 20C at the tip end portion 10a and thicker than the conductive pattern 20C at the tip end portion 10a. Similarly, the conductive pattern 20D at the base end portion 10b is wider than the conductive pattern 20D at the tip end portion 10a and thicker than the conductive pattern 20D at the tip end portion 10a.

An interval between the conductive pattern 20C and the conductive pattern 20D decreases from the base end portion 10b to the tip end portion 10a as illustrated in FIG. 7. That is, a pitch is wider at the base end portion 10b. The pitch decreases toward the tip end portion 10a. In this case, not only manufacturing by the above-described semi-additive method but also manufacturing by a subtractive method as described later can be employed.

The pitch between two conductive patterns in the first variation is 20 to 30 μm, for example. The pitch between two conductive patterns in the second variation is, for example, 30 to 50 μm at the tip end portion and 50 to 70 μm at the base end portion.

Note that the number of conductive patterns is not limited to two conductive patterns. The number of conductive patterns can be determined as necessary.

Next, examples of the method for manufacturing the catheter flexible printed wiring boards 1A, 1B according to the first and second variations will be described in a sequential order. In the first variation, the semi-additive method is used. In the second variation, the subtractive method is used. Note that the manufacturing methods described below will be set forth merely as examples. The manufacturing method is not specifically limited.

<Method for Manufacturing Catheter Flexible Printed Wiring Board 1A>

Some examples of the method for manufacturing the catheter flexible printed wiring board 1A according to the first variation will be described with reference to FIGS. 8A to 8C and FIG. 9.

First, the long flexible insulating base member 10 having the tip end portion 10a and the base end portion 10b and having a seed layer 40 formed on a surface is prepared. In this example, a roll-shaped flexible insulating base member 10R1 having a seed layer formed on a surface and rolled up in rolls R1, R2 is prepared. The flexible insulating base member 10R1 is made of polyimide (a thickness of 25 to 50 μm), for example. Note that the roll-shaped flexible insulating base member 10R1 is equivalent to multiple flexible insulating base members 10 connected to each other at predetermined intervals such that a longitudinal direction of each flexible insulating base member 10 is along a flow direction MD. The roll-shaped flexible insulating base member 10R1 is taken as an assembly of the multiple flexible insulating base members 10.

The seed layer 40 is a conductive layer necessary for performing electroplating. The seed layer 40 includes an anchor layer and a copper seed layer. The anchor layer is, before formation of the copper seed layer, formed on the surface of the flexible insulating base member 10 to enhance adhesion of the copper seed layer. The anchor layer is formed by sputtering, for example. The thickness of the anchor layer is about several nanometers. The anchor layer is, for example, made of nickel (Ni), nickel-chrome (Ni/Cr), or chrome-copper (Cr/Cu). The copper seed layer is, for example, formed on the anchor layer by vapor deposition or sputtering. The thickness of the copper seed layer is about 0.3 to 3 μm.

The flexible insulating base member 10R1 may be prepared in such a manner that the flexible insulating base member 10 is formed on prepared extremely-thin copper foil (e.g., a thickness of 1.5 to 3.0 μm). For example, the flexible insulating base member 10R1 may be a copper clad laminate (CCL) having two layers and formed in such a manner that a polyimide film is laminated on one surface of the extremely-thin copper foil by thermal compression bonding. Alternatively, the flexible insulating base member 10R1 may be a copper clad laminate having two layers and formed in such a manner that polyimide dissolved in a solvent is applied to one surface of the extremely-thin copper foil (a cast method). As another alternative, the flexible insulating base member 10R1 may be a copper clad laminate having an adhesive layer provided between the extremely-thin copper foil and a polyimide film.

Next, a resist layer made of photosensitive resin is formed on the seed layer 40. The resist layer may be, for example, formed in such a manner that a dry film is laminated on the seed layer 40. Alternatively, the resist layer may be formed in such a manner that resist paste is applied onto the seed layer 40.

Figure 8A:
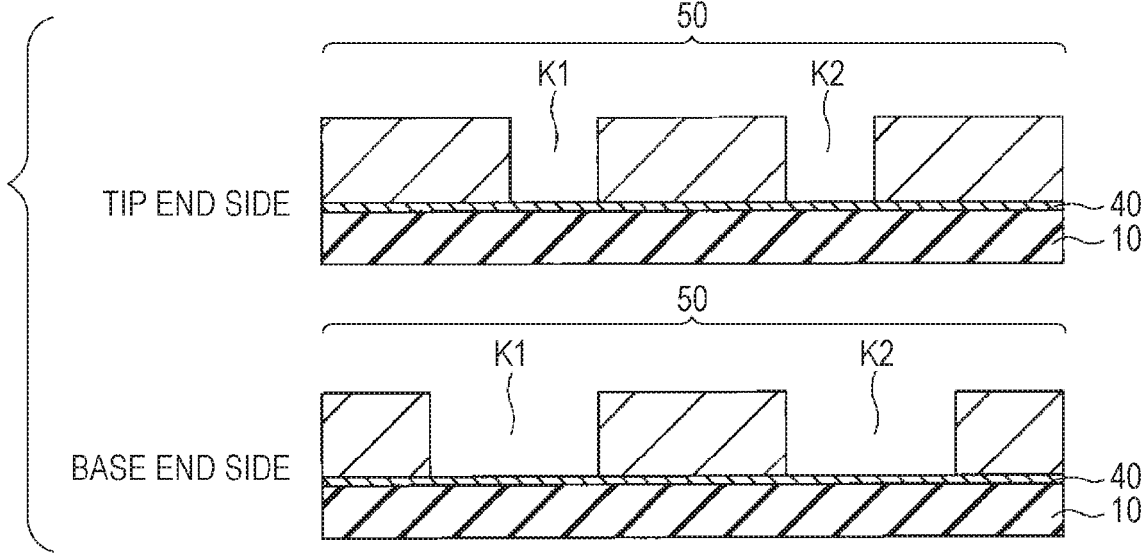
FIG. 8A is a sectional view for describing a step in the method for manufacturing a catheter flexible printed wiring board by a semi-additive method.

Next, as illustrated in FIG. 8A, the resist layer formed on the seed layer 40 is patterned by a well-known photofabrication technique. In this manner, a resist mask 50 having openings K1, K2 is formed. The openings K1, K2 are each provided at portions where the conductive patterns 20A, 20B are formed. The openings K1, K2 extend from the tip end portion 10a to the base end portion 10b. Moreover, the widths of the openings K1, K2 at the base end portion 10b are greater than the widths of the openings K1, K2 at the tip end portion 10a.

Figure 8B:
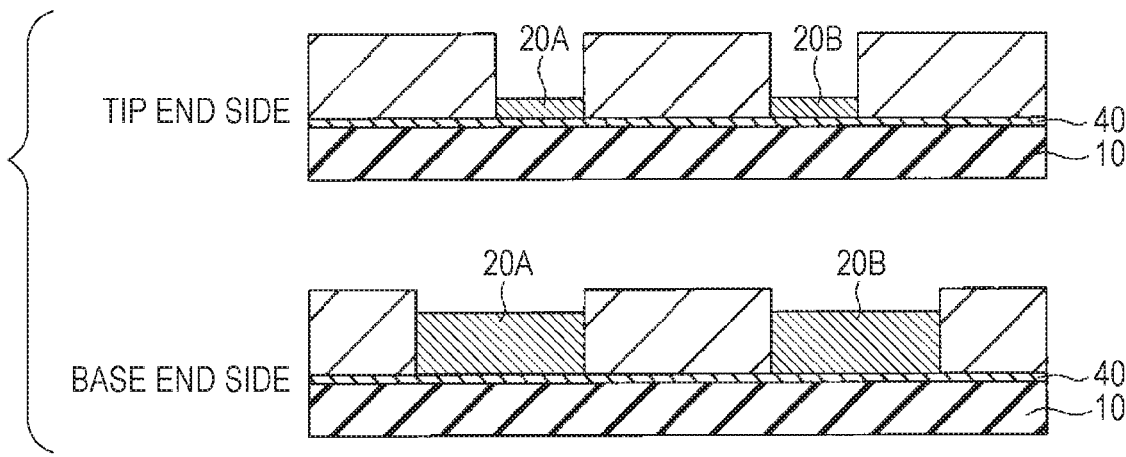
FIG. 8B is a sectional view for describing a step in the method for manufacturing the catheter flexible printed wiring board, FIG. 8B being continued from FIG. 8A.

Next, as illustrated in FIG. 8B, a plated layer is formed on the seed layer 40 exposed in the openings K1, K2 of the resist mask 50 such that a plating thickness at the base end portion 10b is greater than a plating thickness at the tip end portion 10a (a plating step). For example, a copper plated layer is formed by copper electroplating. The plated layer formed at this step forms the conductive patterns 20A, 20B described above.

The plated layer having different thicknesses along an extension direction is formed. Thus, in the present embodiment, a horizontally-conveying web plating equipment 100 (see FIG. 9) having multiple cells (also called plating tanks or chambers) continuously provided along a predetermined direction (the flow direction MD) is used. In the example illustrated in FIG. 9, 16 cells C1 to C16 are provided between the roll R1 and the roll R2. A cathode roller (not shown) may be provided between adjacent ones of the cells. Alternatively, the cathode roller may be provided only in the vicinity of an inlet of the horizontally-conveying web plating equipment 100. The cathode roller is electrically connected to a negative electrode of a DC power source (not shown). In addition, the cathode roller is provided in contact with the surface of the flexible insulating base member 10R1. Note that a conductive brush may be provided instead of the cathode roller.

In the case of providing the cathode roller between adjacent ones of the cells, a resistance value between the cathode roller and the flexible insulating base member 10R1 can be decreased. Thus, a thick plated layer can be easily formed. Further, the cathode roller of each cell and anode electrodes of the cells C1 to C16 can be connected to individual DC power sources. Thus, current and voltage values of each cell can be managed separately.

The flexible insulating base member 10R1 is rolled out of the roll R1, and is conveyed along the flow direction MD. Thereafter, the flexible insulating base member 10R1 is rolled up in the roll R2. Note that the number of cells is not limited to the number in this example. The number of cells can be determined as necessary.

The anode electrode (not shown) connected to a positive electrode of the DC power source is provided in each of the cells C1 to C16. Moreover, the cells C1 to C16 hold an electrolyte (e.g., CuSO4). The entire length (the total length in the flow direction MD) L1 of the multiple cells is substantially equal to or longer than the length of the flexible insulating base member 10 (i.e., one product region of the flexible insulating base member 10R1).

While the flexible insulating base member 10R1 rolled out of the roll R1 is passing through the cells C1 to C16, the plated layer is formed on the flexible insulating base member 10R1. Thereafter, the flexible insulating base member 10R1 is rolled up in the roll R2. The negatively-charged flexible insulating base member 10R1 passes through the cells C1 to C16, and in this manner, the plated layer is formed on the seed layer 40 exposed in the openings K1, K2.

More specifically, a portion (the product region), which is equivalent to the flexible insulating base member 10, of the flexible insulating base member 10R1 having the resist mask 50 is conveyed into the horizontally-conveying web plating equipment 100 from a base end portion 10b side. Then, when the base end portion 10b reaches the downstreammost cell C16, plating current is stopped. In this state, the portion equivalent to the flexible insulating base member 10 is promptly and directly taken out of the horizontally-conveying web plating equipment 100. In this manner, the plated layer formed thicker on the base end portion 10b side than a tip end portion 10a side can be obtained.

Note that a plating current value of each of the cells C1 to C16 may be set higher toward a downstream side (a roll R2 side). For example, the current value of each cell is set such that the thickness of the plated layer reaches the maximum target value at the cell C16. Thus, the thickness of the plated layer on the base end portion 10b side can be formed greater. As a result, low resistance of the conductive patterns 20A, 20B can be realized.

Moreover, at at least the tip end portion 10a, the thickness of the plated layer is preferably equal to or less than 1.5 times as large as the width of the plated layer, and more preferably equal to or less than 1.0 times. Thus, structural stability of the plated layer at the tip end portion 10a can be ensured.

Figure 8C:
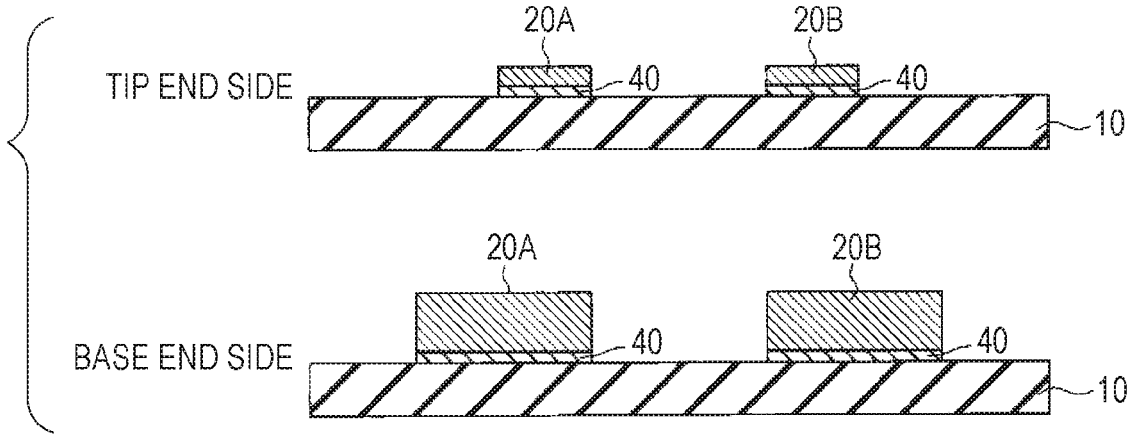
FIG. 8C is a sectional view for describing a step in the method for manufacturing the catheter flexible printed wiring board, FIG. 8C being continued from FIG. 8B.
Figure 9:
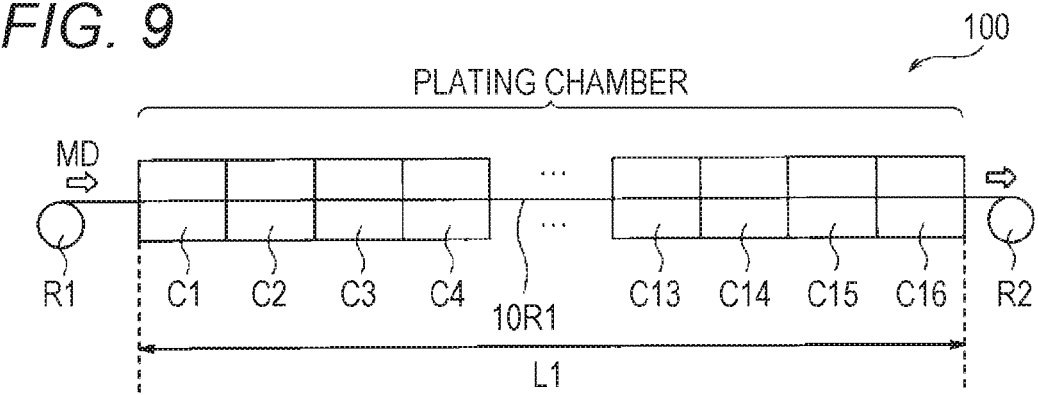
FIG. 9 is a view for describing the step of forming a plated layer by means of a horizontally-conveying web plating equipment.

After formation of the plated layer, the resist mask 50 and the seed layer 40 therebelow are removed as illustrated in FIG. 8C. More specifically, after stripping of the resist mask 50, the seed layer 40 is removed by flash etching. Etchant having selectivity to metal contained in the seed layer 40 is used for removal of the seed layer 40. For example, in a case where the anchor layer of the seed layer 40 contains nickel, a liquid mixture of nitric acid solubilizing nickel and sulfuric acid solubilizing copper of the copper seed layer is used as the etchant. In a case where the seed layer 40 is the above-described extremely-thin copper foil including no anchor layer, dissimilar metal etching is not necessary. Thus, preferable etchant is persulfuric acid soda, for example.

Thereafter, surface treatment, formation of a surface protection film, and outline machining are performed for the conductive patterns 20A, 20B, for example. In outline machining, the flexible insulating base member 10 is processed such that the width thereof decreases from the base end portion 10b to the tip end portion 10a. Outline machining is performed using a laser machining device, so that the flexible insulating base member 10R1 can be easily processed into a thin linear shape.

Note that formation of the conductive patterns 20A, 20B is not limited to the above-described method. A partial plating method or a separated sheet plating method can be used for formation of the conductive patterns 20A, 20B. First, the case of forming the conductive patterns 20A, 20B by means of the partial plating method will be described. In this case, a plating process is performed in such a manner that the flexible insulating base member passes through the above-described horizontally-conveying web plating equipment 100 multiple times. In this manner, a conductive pattern whose thickness increases toward the base end portion 10b side is formed. More specifically, the conductive patterns 20A, 20B are formed by the following method.

The flexible insulating base member 10R1 passes through the horizontally-conveying web plating equipment 100 without stopping the plating current. Thus, a thin plated layer is formed from the tip end portion 10a to the base end portion 10b (the plating step).

Next, the plated layer on the tip end portion 10a side is covered with a plating inhibitor (e.g., a tape or a resist) (a covering step). Then, by the plating step performed again, the plated layer on the base end portion 10b side is thickened. Thereafter, the plating inhibitor is removed (a removal step). A series of these steps (the plating step, the covering step, and the removal step) is performed multiple times while a region covered with the plating inhibitor is gradually expanded from the tip end portion 10a side toward the base end portion 10b side. In this manner, the conductive patterns 20A, 20B whose thicknesses increase in a stepwise manner from the tip end portion 10a side toward the base end portion 10b side can be formed.

Figure 10A:
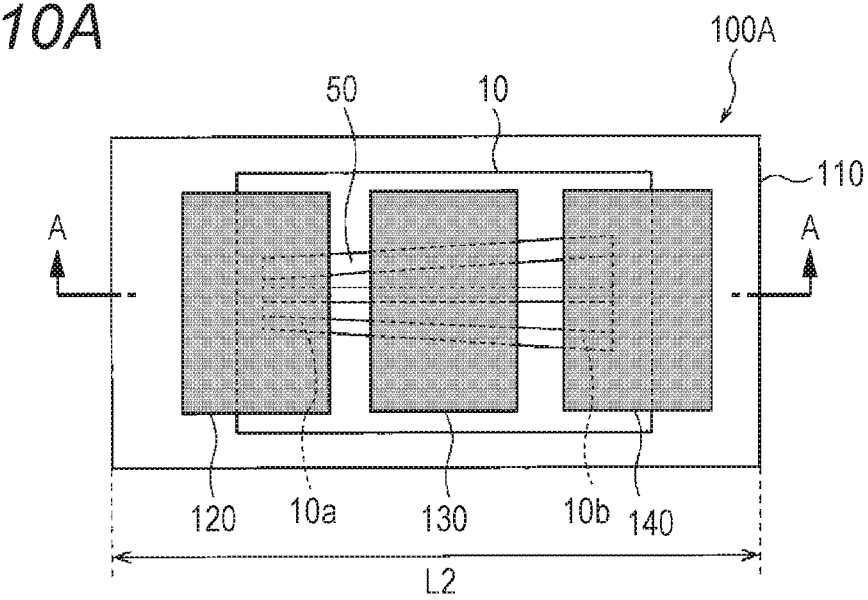
FIGS. 10A and 10B are views for describing the step of forming a plated layer by means of a separated sheet plating equipment.

Next, the case of the forming the conductive patterns 20A, 20B by means of the separated sheet plating method will be described. In this case, the plating process is performed for each sheet of the flexible insulating base member 10 (see FIG. 8A) having the resist mask 50 formed on the surface. Such a plating process is performed using a separated sheet plating equipment 100A. As illustrated in FIG. 10A, the entire length L2 of the separated sheet plating equipment 100A (a cell 110) is longer than the length of the flexible insulating base member 10. The entire length L2 may be substantially equal to the length of the flexible insulating base member 10 (one product region).

Figure 10B:
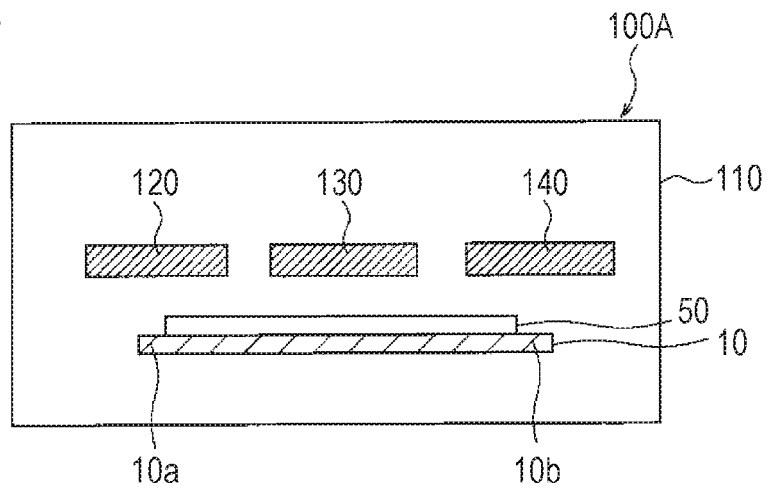

As illustrated in FIGS. 10A and 10B, the separated sheet plating equipment 100A includes the cell 110 extending in a predetermined direction, and multiple anode electrodes 120, 130, 140 provided in the cell 110. The not-shown cell 110 holds an electrolyte (not shown) such as $CuSO_4$, for example. Each of the multiple anode electrodes 120, 130, 140 is connected to the positive electrode of the DC power source (not shown). The multiple anode electrodes 120, 130, 140 are provided next to each other along a direction (the horizontal direction of FIG. 10A) in which the cell 110 extends.

Different positive voltages are applied to the anode electrodes 120, 130, 140. More specifically, as illustrated in FIGS. 10A and 10B, the flexible insulating base member 10 having the resist mask 50 is arranged in the cell 110 of the separated sheet plating equipment 100A, and is negatively charged. In this state, the different positive voltages are applied to the anode electrodes 120, 130, 140 such that a plating current density (the density of current flowing in the flexible insulating base member 10 from the anode electrode) increases from the tip end portion 10a side toward the base end portion 10b side. For example, the voltage to be applied increases in the order of the anode electrode 140, the anode electrode 130, and the anode electrode 120. Thus, the conductive patterns 20A, 20B whose thicknesses increase from the tip end portion 10a side toward the base end portion 10b side can be formed.

Figure 11A:
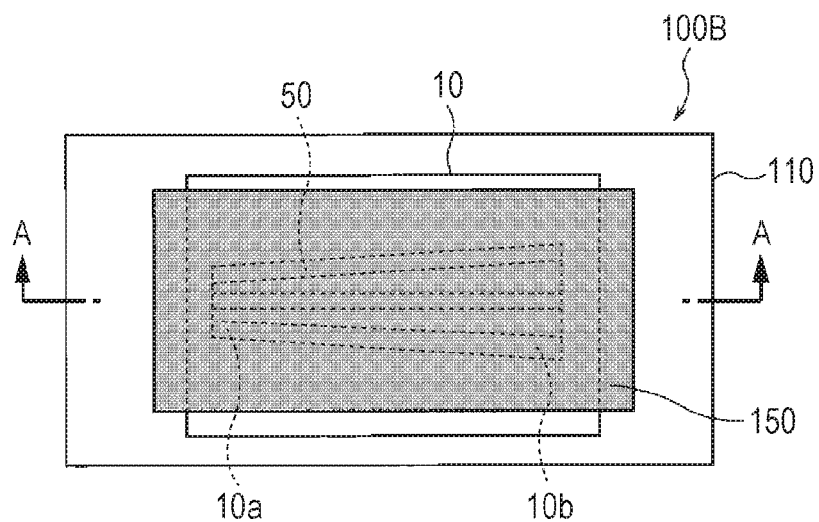
FIGS. 11A and 11B are views for describing the step of forming a plated layer by means of a separated sheet plating equipment.
Figure 11B:
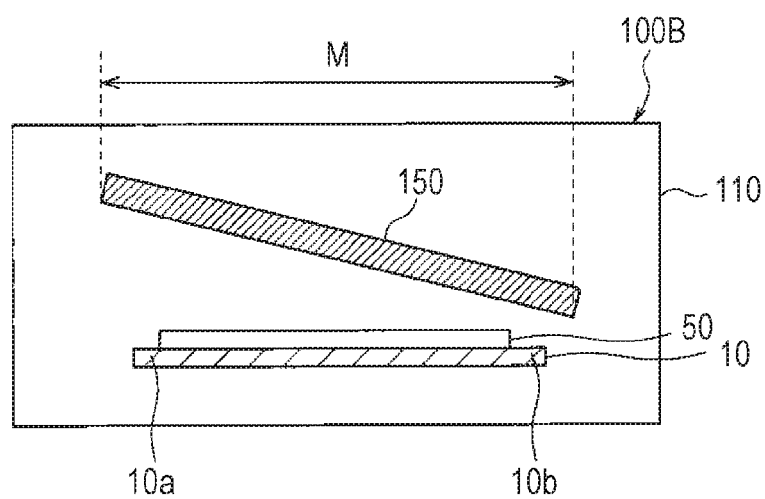

Note that instead of providing the multiple anode electrodes in the separated sheet plating equipment, an anode electrode may be arranged inclined with respect to the flexible insulating base member 10 as illustrated in FIGS. 11A and 11B. That is, a separated sheet plating equipment 100B according to a variation includes the cell 110 extending in a predetermined direction, and an anode electrode 150 arranged in the cell 110. As illustrated in FIG. 11B, the length M of the anode electrode 150 projected on the flexible insulating base member 10 is longer than the length of the flexible insulating base member 10. The projection length M may be substantially equal to the length of the flexible insulating base member 10 (one product region).

The anode electrode 150 of the separated sheet plating equipment 100B is inclined with respect to the flexible insulating base member 10 arranged in the cell 110 such that a distance (an inter-electrode distance) between the flexible insulating base member 10 and the anode electrode 150 decreases from the tip end portion 10a side toward the base end portion 10b side. The anode electrode 150 is provided in the cell 110, and therefore, solution resistance decreases and the plating current density increases from the tip end portion 10a side toward the base end portion 10b side. As a result, a plated layer whose plating thickness is smaller on the tip end portion 10a side and is greater on the base end portion 10b side can be formed.

Figure 12A:
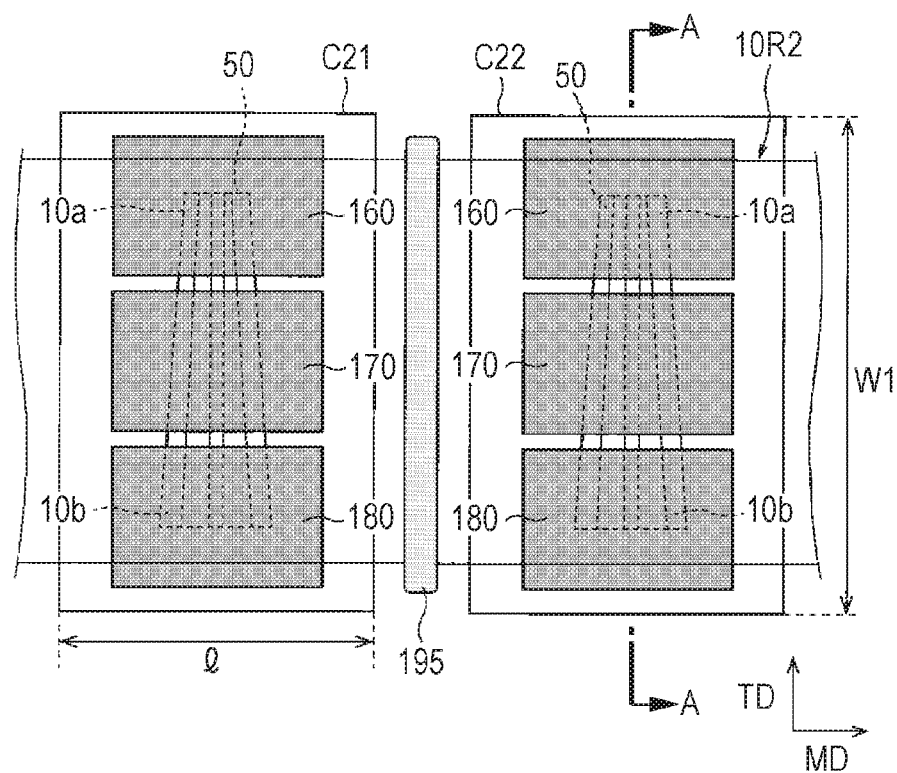
FIGS. 12A and 12B are views for describing the step of forming a plated layer by a roll-to-roll method.
Figure 12B:
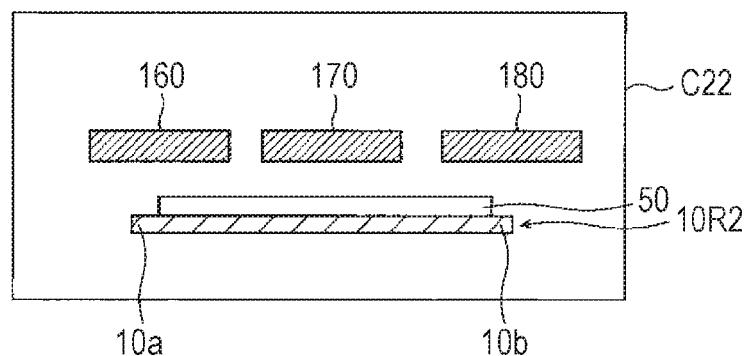

Alternatively, the device having the anode electrode designed as described above may be, as another method, applied to a roll-to-roll method. As illustrated in FIGS. 12A and 12B, the horizontally-conveying web plating equipment has multiple cells C21, C22, . . . continuously provided along the flow direction MD. The width W1 (the length in a direction TD perpendicular to the flow direction MD) of the cells C21, C22, . . . is substantially equal to or longer than the width of a roll-shaped flexible insulating base member 10R2. The width of the flexible insulating base member 10R2 is equivalent to the length of the flexible insulating base member 10 in the longitudinal direction thereof. The length l of each cell C21, C22, . . . is substantially equal to or longer than the width (a length in a lateral direction) of a portion, which is equivalent to the flexible insulating base member 10, of the flexible insulating base member 10R2.

The roll-shaped flexible insulating base member 10R2 is an assembly of the multiple flexible insulating base members 10. The roll-shaped flexible insulating base member 10R2 is equivalent to the multiple flexible insulating base members 10 connected to each other at predetermined intervals such that the lateral direction of each flexible insulating base member 10 is along the flow direction MD. Such an interval is substantially equal to a center distance between adjacent ones of the cells, for example. In each product region, the resist mask 50 is formed to extend in a cell width direction.

A cathode roller 195 may be provided between adjacent ones of the cells (see FIG. 12A). Alternatively, the cathode roller 195 may be provided only in the vicinity of the inlet of the horizontally-conveying web plating equipment. The cathode roller 195 is electrically connected to the negative electrode of the DC power source (not shown). In addition, the cathode roller 195 contacts a surface of the flexible insulating base member 10R2. Note that a conductive brush may be provided instead of the cathode roller.

The cathode roller 195 is provided between adjacent ones of the cells so that a resistance value between the cathode roller and the flexible insulating base member 10R2 can be decreased. Thus, a thick plated layer can be easily formed. Further, the cathode roller of each cell and anode electrodes of the cells C21, C22, . . . can be connected to individual DC power sources. Thus, current and voltage values of each cell can be separately managed.

As illustrated in FIGS. 12A and 12B, multiple anode electrodes 160, 170, 180 are provided in each cell C21, C22 . . . . Each of the anode electrodes 160, 170, 180 is connected to the positive electrode of the DC power source (not shown). The anode electrodes 160, 170, 180 are arranged next to each other along the direction (the direction TD) perpendicular to the direction (the direction MD) in which the multiple cells are continuously provided.

Different positive voltages are applied to the anode electrodes 160, 170, 180. More specifically, as illustrated in FIGS. 12A and 12B, the flexible insulating base member 10R2 is rolled out of a roller such that the resist mask 50 is arranged at a predetermined position of each cell. The flexible insulating base member 10R2 is negatively charged by the cathode roller 195. In this state, the different positive voltages are applied to the anode electrodes 160, 170, 180 such that the plating current density increases from the tip end portion 10*a* side toward the base end portion 10*b* side. In this manner, the conductive patterns 20A, 20B whose thicknesses increase from the tip end portion 10*a* side toward the base end portion 10*b* side can be, as described above, simultaneously formed in each cell. The roll-to-roll method is employed, so that productivity of the catheter flexible printed wiring board can be improved.

Figure 13A:
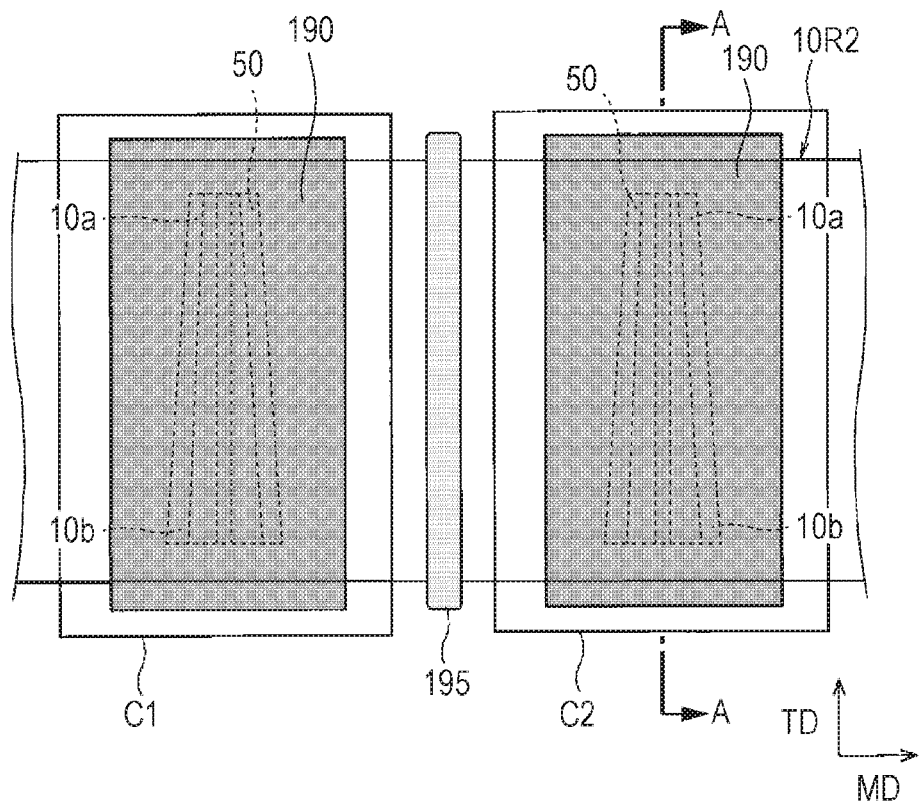
FIGS. 13A and 13B are views for describing the step of forming a plated layer by the roll-to-roll method.
Figure 13B:
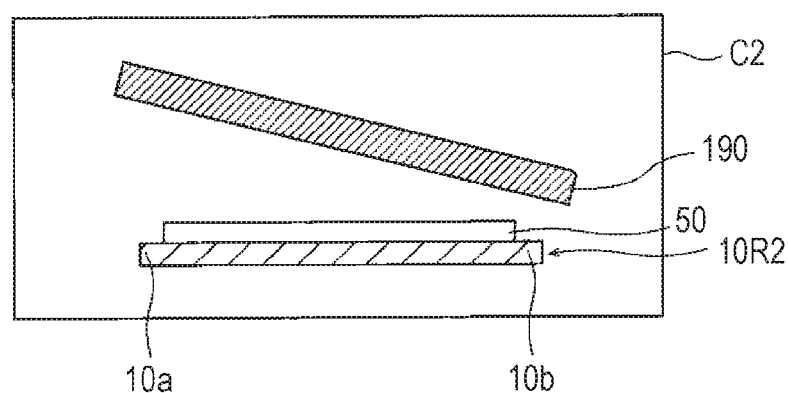

An anode electrode 190 as an inclined electrode similar to the above-described anode electrode 150 may be used as an anode electrode in each of the cells C21, C22, . . . instead of the multiple anode electrodes 160, 170, 180. In this case, as illustrated in FIGS. 13A and 13B, the anode electrode 190 is inclined with respect to the flexible insulating base member 10R2 such that a distance (an inter-electrode distance) between the flexible insulating base member 10R2 and the anode electrode 190 decreases from the tip end portion 10*a* side toward the base end portion 10*b* side. The length of the anode electrode 190 projected on the flexible insulating base member 10R2 is longer than the width of the flexible insulating base member 10R2. The projection length may be substantially equal to the width of the flexible insulating base member 10R2. Even in the case of using the anode electrode 190, the conductive patterns 20A, 20B whose thicknesses increase from the tip end portion 10*a* side toward the base end portion 10*b* side can be formed as described above.

<Method for Manufacturing Catheter Flexible Printed Wiring Board 1B>

Next, one example of the method for manufacturing the catheter flexible printed wiring board 1B according to the second variation will be described. Two manufacturing methods will be described herein. One method is the method (a first manufacturing method) for forming the conductive patterns 20C, 20D by uniformly performing etching after formation of a plated layer with different thicknesses. The other method is the method (a second manufacturing method) for forming the conductive patterns 20C, 20D by performing half etching for metal foil (e.g., copper foil) with a constant thickness.

First, the first manufacturing method will be described with reference to FIGS. 14A and 14B. The long flexible insulating base member 10 having the tip end portion 10*a* and the base end portion 10*b* is prepared. For example, a roll-shaped flexible insulating base member is prepared.

Figure 14A:
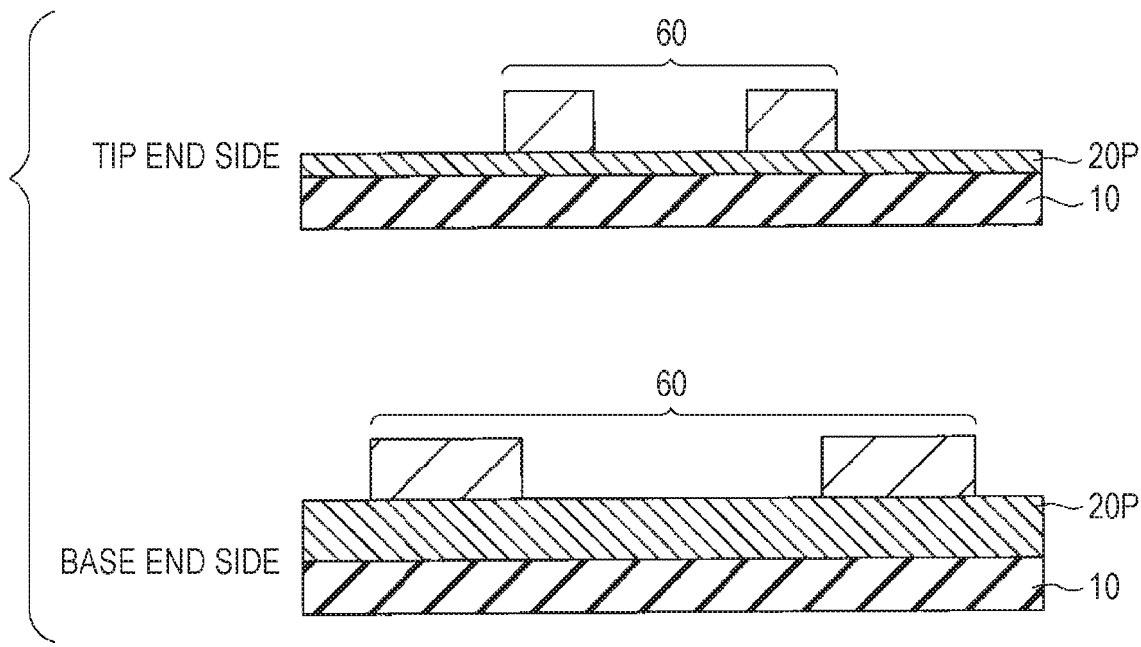
FIG. 14A is a sectional view for describing a step in a first catheter flexible printed wiring board manufacturing method by a subtractive method.

Next, as illustrated in FIG. 14A, a plated layer 20P is formed on the flexible insulating base member 10 such that a plating thickness at the base end portion 10*b* is greater than a plating thickness at the tip end portion 10*a* (a plating step). For example, the plated layer 20P is formed using the above-described horizontally-conveying web plating equipment. Note that the plated layer 20P may be formed by partial plating or half etching for partially thinning the plated layer by etching.

Next, as illustrated in FIG. 14A, a resist mask 60 is formed on the plated layer 20P. The resist mask 60 is formed to cover portions where the conductive patterns 20C, 20D are to be formed. More specifically, the resist mask 60 extends from the tip end portion 10*a* to the base end portion 10*b*. Moreover, a width at the base end portion 10*b* is greater than a width at the tip end portion 10*a*.

Figure 14B:
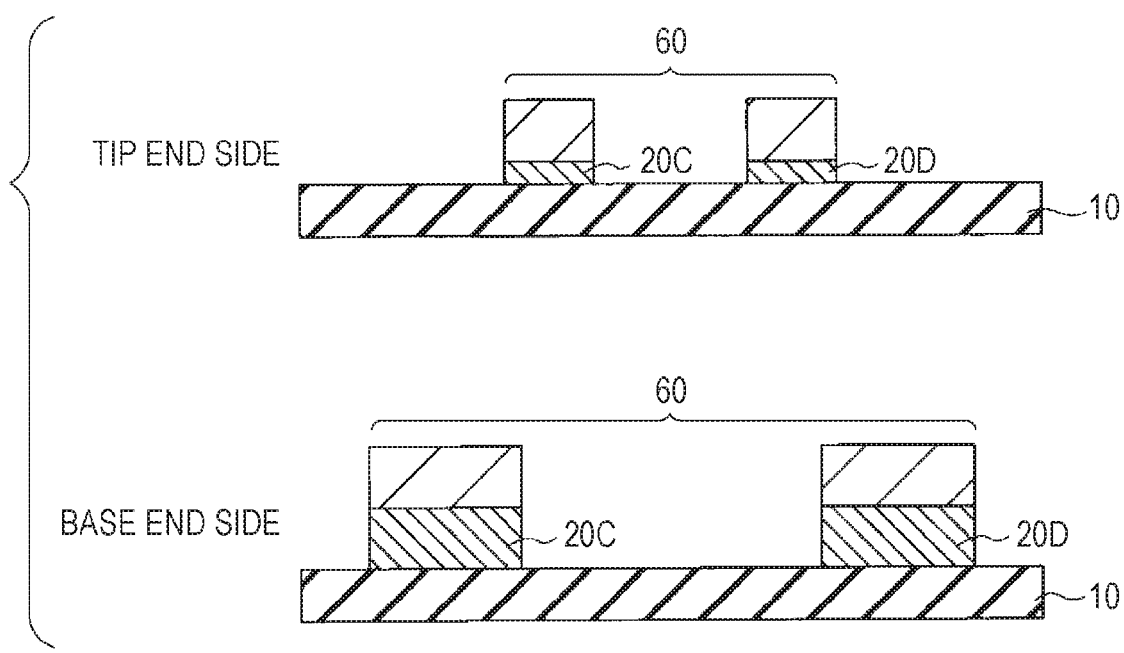
FIG. 14B is a sectional view for describing a step in the first catheter flexible printed wiring board manufacturing method, FIG. 14B being continued from FIG. 14A.

Next, as illustrated in FIG. 14B, a portion of the plated layer 20P uncovered with the resist mask 60 is removed by etching (an etching step). After the etching step, the resist mask 60 is removed.

Thereafter, surface treatment, formation of a surface protection film, and outline machining are performed for the conductive patterns 20C, 20D, for example. As described regarding the method for manufacturing the catheter flexible printed wiring board 1A according to the first variation, in outline machining, laser machining can be suitably used.

Next, the method for manufacturing the catheter flexible printed wiring board 1B by the second manufacturing method for changing an etching amount will be described.

First, a strip-shaped (sheet-shaped) copper clad laminate 18 large enough to hold the catheter flexible printed wiring board 1B is prepared. The copper clad laminate 18 has the flexible insulating base member 10 (e.g., polyimide (a thickness of 25 to 50 μm)) and copper foil 20Q formed on one surface of the flexible insulating base member 10. The copper foil 20Q is rolled copper foil or electrolytic copper foil. The thickness of the copper foil 20Q is selected according to the thicknesses of the conductive patterns 20A, 20B at the base end portion 10*b*. A suitable thickness is 60 to 70 μm, for example.

Next, as in the case of the first manufacturing method, the resist mask 60 is formed on the copper foil 20Q. The resist mask 60 is formed to cover portions where the conductive patterns 20C, 20D are to be formed. More specifically, the resist mask 60 extends from the tip end portion 10*a* to the base end portion 10*b*. The width of the resist mask 60 at the base end portion 10*b* is greater than the width of the resist mask 60 at the tip end portion 10*a*.

Figure 15A:
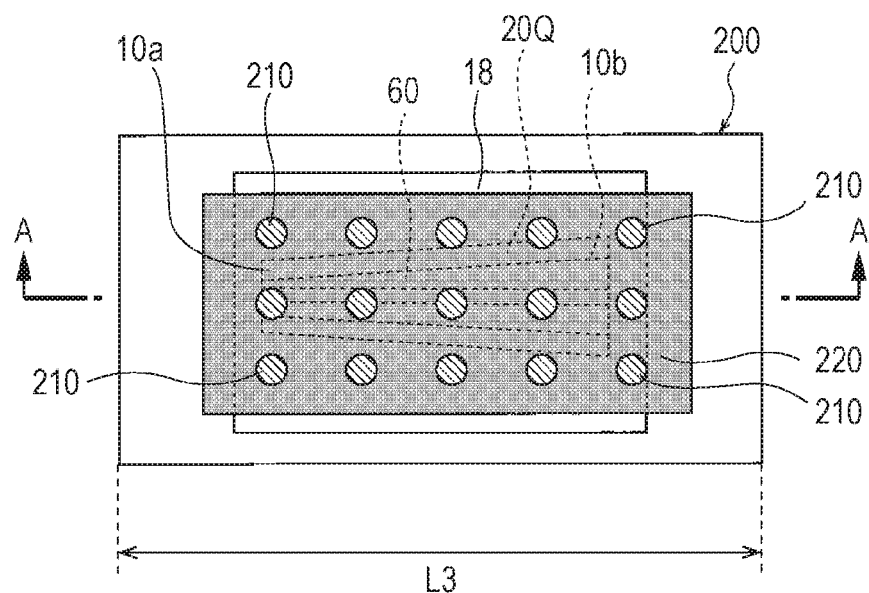
FIGS. 15A and 15B are views for describing the method for manufacturing a catheter flexible printed wiring board by means of a strip half etching device.
Figure 15B:
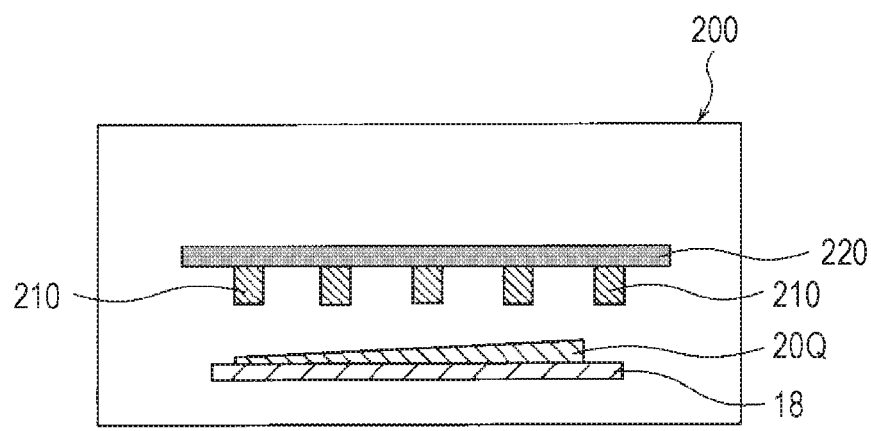

Next, a portion of the copper foil 20Q uncovered with the resist mask 60 is removed by etching (an etching step). More specifically, as illustrated in FIGS. 15A and 15B, the copper foil 20Q of the prepared copper clad laminate 18 is etched such that the thickness of the copper foil 20Q at the base end portion 10b is greater than the thickness of the copper foil 20Q at the tip end portion 10a. As illustrated in FIGS. 15A and 15B, the copper foil 20Q is etched by a strip half etching device 200. Note that the entire length L3 of the strip half etching device 200 (a chamber) is substantially equal to or longer than the flexible insulating base member 10.

Multiple spray portions 210 are arranged at the same height in the chamber of the strip half etching device 200. The multiple spray portions 210 are provided on a spray installation board 220 at certain intervals along an extension direction of the strip half etching device 200. In an example of FIGS. 15A and 15B, the spray portions 210 are also provided at certain intervals in a width direction of the strip half etching device 200.

The spray portions 210 spray an etching solution (e.g., a ferric chloride solution) toward the copper foil 20Q of the copper clad laminate 18. The spray pressure of the etching solution from the spray portions 210 is set to increase from the base end portion 10b side toward the tip end portion 10a side. That is, the spray pressure is adjusted such that the amount of the etching solution sprayed from the spray portions 210 increase from the base end portion 10b side toward the tip end portion 10a side. After adjustment of the spray pressure, the copper clad laminate 18 placed in the strip half etching device 200 is half-etched. Thus, the copper foil 20Q is more etched on the tip end portion 10a side than on the base end portion 10b side. As a result, the conductive patterns 20A. 20B formed thicker on the base end portion 10b side than on the tip end portion 10a side are obtained.

Figure 16A:
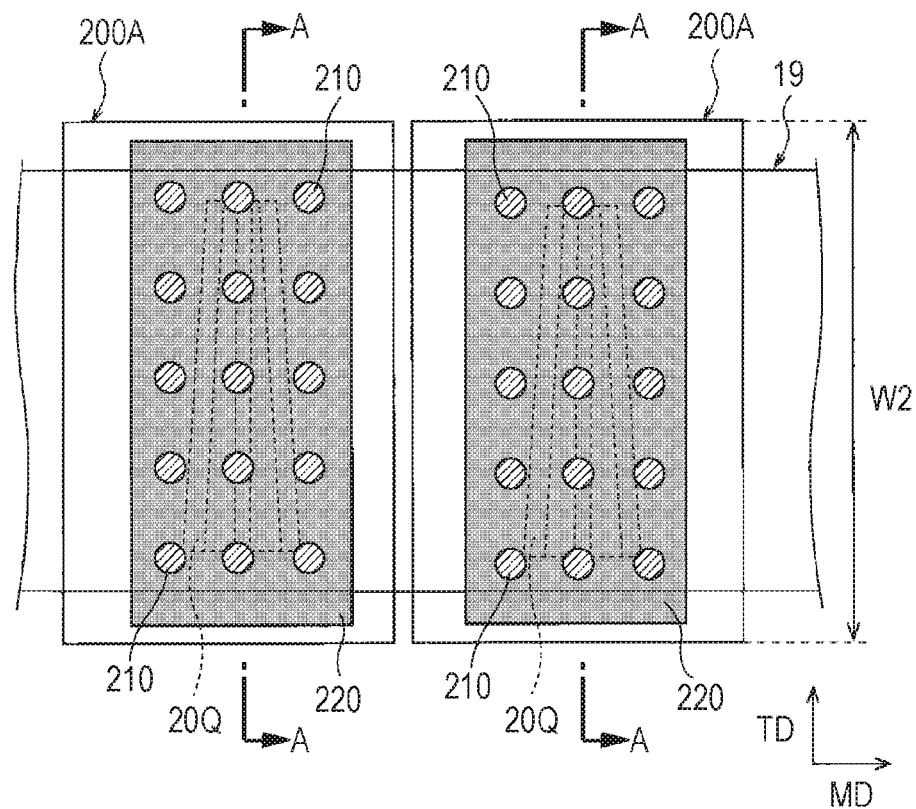
FIGS. 16A and 16B are views for describing the method for manufacturing a catheter flexible printed wiring board by means of a continuous half-etching device.

Note that the separated sheet plating equipment is used in the second manufacturing method. Note that a continuous half-etching device may be used. In this case, the copper foil is continuously half-etched using a roll-shaped copper clad laminate 19. The roll-shaped copper clad laminate 19 to be conveyed into a continuous half-etching device 200A is prepared. Product regions are provided at predetermined intervals at the copper clad laminate 19. The resist mask 60 is formed on each product region. As illustrated in FIG. 16A, the resist mask 60 is formed such that a longitudinal direction thereof is along the direction TD.

Figure 16B:
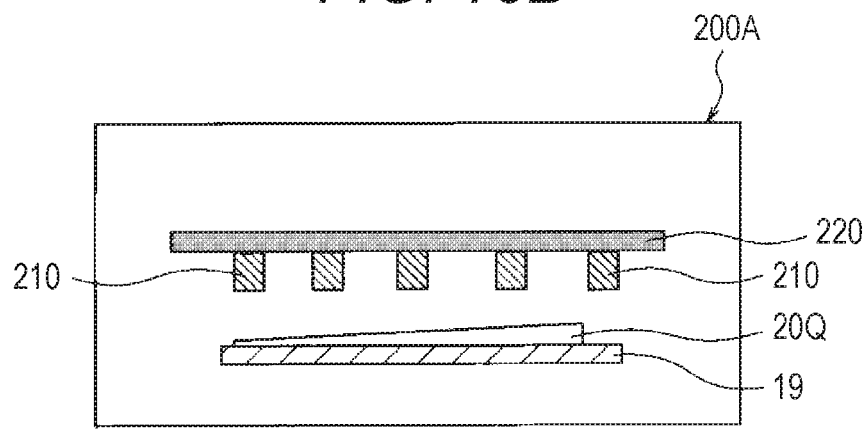

As illustrated in FIGS. 16A and 16B, the width W2 (the length in the direction TD perpendicular to the flow direction MD) of the continuous half-etching device 200A (a chamber) in the direction perpendicular to the flow direction MD of the copper clad laminate 19 is substantially equal to or longer than the width of the roll-shaped copper clad laminate 19.

The continuous half-etching device 200A has the multiple spray portions 210 provided on the spray installation board 220. The spray portions 210 are arranged at the same height in the chamber, and are provided at certain intervals along the direction TD. More specifically, the multiple spray portions 210 are arranged along the direction TD such that multiple ones of the spray portions 210 are present in an area from the tip end portion 10a to the base end portion 10b upon etching of the copper foil 20Q. The spray pressure of the spray portions 210 is adjusted such that the spray amount of the etching solution increases from the base end portion 10b toward the tip end portion 10a.

Note that in an example of FIGS. 16A and 16B, the spray portions 210 are also provided at certain intervals in the flow direction MD. The spray pressure of the spray portions 210 arranged along the flow direction MD is adjusted such that the same spray amount of the etching solution is provided.

When the roll-shaped copper clad laminate 19 performs etching by means of the above-described continuous half-etching device 200A, etching of the copper foil 20Q on the tip end portion 10a side more advances than etching of the copper foil 20Q on the base end portion 10b side. As a result, the conductive patterns 20C, 20D formed thicker on the base end portion 10b side than the tip end portion 10a side can be obtained. Using the continuous half-etching device, half etching can be continuously performed as compared to the strip half-etching device. Thus, the productivity can be improved.

According to the catheter flexible printed wiring board manufacturing methods according to the above-described first and second variations, low resistance of the conductive patterns 20A, 20B (the conductive patterns 20C, 20D) can be realized while the thicknesses of the conductive patterns 20A, 20B (the conductive patterns 20C, 20D) at the tip end portion 10a can be reduced.

This can suppress the sections of the conductive patterns 20A, 20B (the conductive patterns 20C, 20D) from being extremely vertically long even in the case of, e.g., a narrow pitch between the conductive patterns 20A, 20B (the conductive patterns 20C, 20D). As a result, structural stability of the conductive patterns 20A, 20B (the conductive patterns 20C, 20D) can be ensured.

Moreover, in the case of the forming the conductive patterns 20C, 20D by the subtractive method, the thicknesses of the conductive patterns 20C, 20D at the tip end portion 10a can be reduced. Thus, removal of the plated layer in the horizontal direction due to overetching can be prevented.

Characteristics of the semi-additive method and the subtractive method as described above can be summarized as follows.

According to the semi-additive method, formation of a fine conductive pattern and narrowing of a gap between the conductive patterns can be realized. Meanwhile, the conductive pattern (a wiring line) is formed from the plated layer containing small copper crystals and therefore having many crystal grain boundaries. Thus, bendability of the conductive pattern is relatively low.

According to the subtractive method, the conductive pattern (the wiring line) is formed from the rolled copper foil containing large copper crystals and therefore having less crystal grain boundaries. Thus, the bendability of the conductive pattern is relatively high. Meanwhile, it is difficult to form a fine conductive pattern and narrow the gap between the conductive patterns.

Second Embodiment

Next, a catheter flexible printed wiring board 1C according to a second embodiment of the present disclosure will be described with reference to FIG. 17. One of differences between the present embodiment and the first embodiment is that not an electrode for ablation but a head portion for mounting various sensors and the like is provided at a tip end portion of the catheter flexible printed wiring board. Hereinafter, the differences of the second embodiment will be mainly described.

The catheter flexible printed wiring board 1C includes a long flexible insulating base member 10, multiple conductive patterns 20 extending from a base end portion 10b to a tip end portion 10a, and a head portion 11. As in the first embodiment, the catheter flexible printed wiring board 1C of the present embodiment includes, as a base material, the single flexible insulating base member 10. The flexible insulating base member 10 and the conductive patterns 20 are similar to those of the first embodiment, and therefore, detailed description will be omitted.

As illustrated in FIG. 17, the head portion 11 is provided to extend from the tip end portion 10a of the flexible insulating base member 10. Multiple pads 22 for mounting various sensors are provided at the head portion 11. The multiple pads 22 are each electrically connected to the conductive patterns 20. Not-shown various sensors (a temperature sensor, a pressure sensor, an acceleration sensor, an ultrasonic element, and the like) are surface-mounted on the pads 22. Electronic components such as a semiconductor chip may be mounted on the pads 22.

Note that surface treatment using, e.g., gold plating may be performed for surfaces of the pads 22. Moreover, the shape of the pad 22 and the number of pads 22 are not limited to those illustrated in FIG. 17.

According to the second embodiment, even in a case where the width of the conductive pattern 20 at the tip end portion 10a is decreased as in the first embodiment, a resistance value of the conductive pattern 20 can be reduced.

Further, according to the second embodiment, various sensors and the like can be directly mounted on the head portion 11 provided at the tip end portion 10a without use of a connector. As a result, size reduction in a catheter and improvement of productivity of the catheter can be realized.

Third Embodiment

Next, a catheter flexible printed wiring board 1D according to a third embodiment of the present disclosure will be described with reference to FIGS. 18A and 18B. One of differences between the present embodiment and the first embodiment is that the catheter flexible printed wiring board includes multiple flexible printed wiring boards connected to each other. Hereinafter, the differences of the third embodiment will be mainly described.

The catheter flexible printed wiring board 1D includes partial flexible insulating base members 15, 16, 17 and partial conductive patterns 25, 26, 27.

The partial flexible insulating base members 15, 16, 17 correspond to the flexible insulating base member 10 described in the first embodiment. That is, the flexible insulating base member 10 is equivalent to a combination of the partial flexible insulating base member 15, the partial flexible insulating base member 16, and the partial flexible insulating base member 17.

Similarly, the partial conductive patterns 25, 26, 27 are equivalent to the conductive pattern 20 described in the first embodiment. The partial conductive pattern 25 is formed on the partial flexible insulating base member 15. The partial conductive pattern 26 is formed on the partial flexible insulating base member 16. The partial conductive pattern 27 is formed on the partial flexible insulating base member 17.

The partial conductive patterns 25, 26, 27 are made of a conductive material such as copper foil. The conductive material is not limited to the copper foil. Other materials (e.g., silver and aluminum) may be used as the conductive material. The partial conductive patterns 25, 26, 27 may be made of multiple different materials.

As illustrated in FIG. 18B, the partial conductive pattern 25 and the partial conductive pattern 26 are electrically connected to each other via a conductive joint member 91. Similarly, the partial conductive pattern 26 and the partial conductive pattern 27 are electrically connected to each other via a conductive joint member 92. The conductive joint members 91, 92 include, for example, solder or an anisotropic conductive film (ACF).

The partial conductive patterns 25, 26, 27 each have thicknesses t1, t2, t3. The thickness of the partial conductive pattern increases toward a base end portion side. That is, the thickness t2 is greater than the thickness t1. The thickness t3 is greater than the thickness t2. That is, the thicknesses of the partial conductive patterns 25, 26, 27 are in a relationship of t1<t2<t3.

Moreover, as illustrated in FIG. 18A, the width of the partial conductive pattern 27 is greater than that of the partial conductive pattern 26. Further, the width of the partial conductive pattern 26 is greater than that of the partial conductive pattern 25.

As described above, the partial conductive patterns 25, 26, 27 form the conductive pattern 20 described in the first embodiment. That is, the partial conductive patterns 25, 26, 27 are configured such that a base end side of the catheter flexible printed wiring board 1D is wider and thicker than the tip end side thereof.

As described above, in the third embodiment, the multiple flexible printed wiring boards form the catheter flexible printed wiring board 1D. According to the present embodiment, advantageous effects similar to those of the first embodiment can be also obtained. That is, the width of the partial conductive pattern 25 at a tip end portion can be narrowed while the total resistance value of the partial conductive patterns 25, 26, 27 can be reduced.

Based on description above, those skilled in the art can arrive at additional advantageous effects and various modifications of the present embodiments. Note that the aspects of the present disclosure are not limited to each of the above-described embodiments. Components of different embodiments may be combined as necessary. Various additions, changes, and partial deletions can be made to the present embodiments without departing from the conceptual idea and gist of the present disclosure derived from the technical scope of the present disclosure and equivalents thereof.

The flexible printed wiring boards according to the embodiments of the present disclosure may be the following first to tenth catheter flexible printed wiring boards.

The first catheter flexible printed wiring board includes a long flexible insulating base member having a tip end portion and a base end portion, and a conductive pattern formed on the flexible insulating base member and extending from the base end portion toward the tip end portion. The conductive pattern at the base end portion is wider than the conductive pattern at the tip end portion and thicker than the conductive pattern at the tip end portion.

The second catheter flexible printed wiring board is the first catheter flexible printed wiring board in which the width of the conductive pattern increases from the tip end portion toward the base end portion and the thickness of the conductive pattern increases from the tip end portion toward the base end portion.

The third catheter flexible printed wiring board is the first or second catheter flexible printed wiring board in which the thickness of the conductive pattern at the tip end portion is equal to or less than 1.5 times as large as the width of the conductive pattern at the tip end portion.

The fourth catheter flexible printed wiring board is any one of the first to third catheter flexible printed wiring boards in which the width of the flexible insulating base member decreases from the base end portion toward the tip end portion.

The fifth catheter flexible printed wiring board is any one of the first to fourth catheter flexible printed wiring boards in which an electrode is attached to a tip end of the conductive pattern and a pad electrically connected to a high-frequency generation device is provided at a base end of the conductive pattern.

The sixth catheter flexible printed wiring board is any one of the first to fifth catheter flexible printed wiring boards further including a head portion which extends from the tip end portion and which has the pad electrically connected to the conductive pattern and provided for mounting a sensor.

The seventh catheter flexible printed wiring board is any one of the first to sixth catheter flexible printed wiring boards in which a first conductive pattern and a second conductive pattern are, as the conductive pattern, formed on the flexible insulating base member and an interval between the first conductive pattern and the second conductive pattern is substantially constant.

The eighth catheter flexible printed wiring board is any one of the first to sixth catheter flexible printed wiring boards in which a first conductive pattern and a second conductive pattern are, as the conductive pattern, formed on the flexible insulating base member and an interval between the first conductive pattern and the second conductive pattern decreases from the base end portion toward the tip end portion.

The ninth catheter flexible printed wiring board is any one of the first to eighth catheter flexible printed wiring boards in which the flexible insulating base member is integrated and is not configured such that multiple flexible printed wiring boards are connected to each other along a longitudinal direction.

The tenth catheter flexible printed wiring board is any one of the first to eighth catheter flexible printed wiring boards in which the flexible insulating base member has a first partial flexible insulating base member and a second partial flexible insulating base member, a first partial conductive pattern formed on the first partial flexible insulating base member has a first thickness, a second partial conductive pattern formed on the second partial flexible insulating base member and electrically connected to the first partial conductive pattern has a second thickness greater than the first thickness, and the first partial conductive pattern and the second partial conductive pattern form the conductive pattern.

The methods for manufacturing the flexible printed wiring boards according to the embodiments of the present disclosure may be the following first to sixth catheter flexible printed wiring board manufacturing methods.

The first catheter flexible printed wiring board manufacturing method is a catheter flexible printed wiring board manufacturing method including the step of preparing a long flexible insulating base member having a tip end portion and a base end portion and having a seed layer on a surface; the step of patterning a resist layer formed on the seed layer to form a resist mask provided with an opening extending from the tip end portion toward the base end portion, the width of the opening at the base end portion being greater than the width of the opening at the tip end portion; the step of forming a plated layer on the seed layer exposed in the opening of the resist mask such that a plating thickness at the base end portion is greater than a plating thickness at the tip end portion; and the step of removing the resist mask and the seed layer therebelow.

The second catheter flexible printed wiring board manufacturing method is the first catheter flexible printed wiring board manufacturing method in which a horizontally-conveying web plating equipment has multiple cells continuously provided along a predetermined direction and is configured such that the entire length of the multiple cells is equal to or longer than the length of the flexible insulating base member, and the horizontally-conveying web plating equipment is used to convey the flexible insulating base member into the horizontally-conveying web plating equipment from a base end portion side and to stop plating current when the base end portion reaches a downstreammost one of the cells and promptly and directly take the flexible insulating base member out of the horizontally-conveying web plating equipment, thereby forming the plated layer.

The third catheter flexible printed wiring board manufacturing method is the second catheter flexible printed wiring board manufacturing method in which a horizontally-conveying web plating equipment has multiple cells continuously provided along a flow direction and is configured such that the width of each cell is equal to or longer than the width of a roll-shaped flexible insulating base member equivalent to multiple flexible insulating base members connected to each other at a predetermined interval with a lateral direction thereof being along the flow direction, and the horizontally-conveying web plating equipment is used to simultaneously form the plated layer at each cell by a roll-to-roll method.

The fourth catheter flexible printed wiring board manufacturing method is the first catheter flexible printed wiring board manufacturing method in which a separated sheet plating equipment has a cell extending in a predetermined direction and multiple anode electrodes provided along the predetermined direction in the cell, and the separated sheet plating equipment is used to apply, in a state in which the flexible insulating base member is arranged and negatively charged in the cell, different positive voltages to the multiple anode electrodes such that a plating current density increases from a tip end portion side toward the base end portion side, thereby forming the plated layer.

The fifth catheter flexible printed wiring board manufacturing method is the first catheter flexible printed wiring board manufacturing method in which a separated sheet plating equipment has a cell extending in a predetermined direction and an anode electrode provided inclined with respect to the flexible insulating base member arranged in the cell such that a distance to the flexible insulating base member decreases from a tip end portion side toward the base end portion side, and the separated sheet plating equipment is used to form the plated layer.

The sixth catheter flexible printed wiring board manufacturing method is a catheter flexible printed wiring board manufacturing method including the step of preparing a long flexible insulating base member having a tip end portion and a base end portion and a metal-clad laminate having metal foil on a surface of the flexible insulating base member; the step of forming a resist mask extending from the tip end portion to the base end portion on the metal foil and having a greater width at the base end portion than a width at the tip end portion; the step of removing, by etching, a portion of the metal foil uncovered with the resist mask, the metal foil being etched such that the thickness of the metal foil at the base end portion is greater than the thickness of the metal foil at the tip end portion; and the step of removing the resist mask.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A catheter flexible printed wiring board comprising:
   a long flexible insulating base member having a tip end portion and a base end portion; and
   a first conductive pattern formed only on one surface of the flexible insulating base member and extending from the base end portion to the tip end portion,
   wherein the first conductive pattern at the base end portion is wider than the first conductive pattern at the tip end portion and thicker than the first conductive pattern at the tip end portion, and
   a thickness of the flexible insulating base member is constant from the base end portion to the tip end portion.

2. The catheter flexible printed wiring board according to claim 1, wherein
   a width of the first conductive pattern increases from the tip end portion toward the base end portion, and
   a thickness of the first conductive pattern increases from the tip end portion toward the base end portion.

3. The catheter flexible printed wiring board according to claim 1, wherein
   a thickness of the first conductive pattern at the tip end portion is equal to or less than 1.5 times as large as a width of the first conductive pattern at the tip end portion.

4. The catheter flexible printed wiring board according to claim 1, wherein
   a width of the flexible insulating base member decreases from the base end portion toward the tip end portion.

5. The catheter flexible printed wiring board according to claim 1, wherein
   an electrode is attached to a tip end of the first conductive pattern, and
   a pad electrically connected to a high-frequency generation device is provided at a base end of the first conductive pattern.

6. The catheter flexible printed wiring board according to claim 1, further comprising:
   a head portion having a pad for mounting a sensor,
   wherein the head portion extends from the tip end portion, and
   the pad is electrically connected to the first conductive pattern.

7. The catheter flexible printed wiring board according to claim 1, further comprising:
   a second conductive pattern, wherein
   the first conductive pattern and the second conductive pattern are formed only on one surface of the flexible insulating base member, and
   an interval between the first conductive pattern and the second conductive pattern is substantially constant.

8. The catheter flexible printed wiring board according to claim 1, further comprising:
   a second conductive pattern, wherein
   the first conductive pattern and the second conductive pattern are formed only on one surface of the flexible insulating base member, and
   an interval between the first conductive pattern and the second conductive pattern decreases from the base end portion toward the tip end portion.

9. The catheter flexible printed wiring board according to claim 1, wherein
   the flexible insulating base member is integrally formed.

* * * * *